(12) United States Patent
Tashiro et al.

(10) Patent No.: US 8,551,959 B2
(45) Date of Patent: Oct. 8, 2013

(54) GLYCOLIPID AND USE THEREOF

(75) Inventors: Takuya Tashiro, Kanagawa (JP); Kenji Mori, Kanagawa (JP); Masao Shiozaki, Kanagawa (JP); Ryusuke Nakagawa, Kanagawa (JP); Masaru Taniguchi, Kanagawa (JP); Hiroshi Watarai, Kanagawa (JP)

(73) Assignee: RIKEN, Wako-shi (JP)

( * ) Notice: Subject to any disclaimer, the term of this patent is extended or adjusted under 35 U.S.C. 154(b) by 260 days.

(21) Appl. No.: 12/934,515

(22) PCT Filed: Mar. 25, 2009

(86) PCT No.: PCT/JP2009/056010
§ 371 (c)(1),
(2), (4) Date: Nov. 23, 2010

(87) PCT Pub. No.: WO2009/119692
PCT Pub. Date: Oct. 1, 2009

(65) Prior Publication Data
US 2011/0104188 A1 May 5, 2011

(30) Foreign Application Priority Data

Mar. 25, 2008 (JP) ................................. 2008-079265

(51) Int. Cl.
*A01N 43/04* (2006.01)
*A61K 31/70* (2006.01)
*A61K 39/00* (2006.01)
*C07H 15/00* (2006.01)
*C07H 19/00* (2006.01)

(52) U.S. Cl.
USPC .................... 514/25; 536/17.9; 424/184.1

(58) Field of Classification Search
None
See application file for complete search history.

(56) References Cited

U.S. PATENT DOCUMENTS

| | | | |
|---|---|---|---|
| 5,849,716 A | 12/1998 | Akimoto et al. | |
| 6,555,372 B1 | 4/2003 | Motoki et al. | |
| 7,273,852 B2 * | 9/2007 | Tsuji et al. ........................ | 514/23 |
| 2002/0032158 A1 | 3/2002 | Tomiyama et al. | |
| 2003/0139351 A1 | 7/2003 | Taniguchi et al. | |
| 2005/0222048 A1 | 10/2005 | Tsuji et al. | |
| 2007/0238673 A1 | 10/2007 | Porcelli | |

| 2007/0238871 A1 | 10/2007 | Tsuji et al. |
|---|---|---|

FOREIGN PATENT DOCUMENTS

| DE | 101 28 250 A1 | 12/2001 |
|---|---|---|
| WO | WO 94/09020 A1 | 4/1994 |
| WO | WO 98/44928 A1 | 10/1998 |
| WO | WO 99/15627 A1 | 4/1999 |
| WO | WO 03/105769 A2 | 12/2003 |

OTHER PUBLICATIONS

Fan et al., Tetrahedron, 61, 2005, pp. 1855-1862.*
Tashiro et al., Tetrahedron Letters, 49, 2008, pp. 6827-6830.*
Anno et al., Tokagaku no Kiso, 11th print: Kabushiki Kaisha Kodansha, pp. 54-57 (Aug. 10, 1995).
Burdin et al., J. Immunol, 161: 3271-3281 (1998).
Fan et al., Tetrahedron, 61: 1855-1862 (2005).
Iijima et al., Bioorganic & Medicinal Chemistry, 6: 1905-1910 (1998).
Karlsson et al., Biochimica et Biophysica Acta, 316: 317-335 (1973).
Kawano et al., Proc. Natl. Acad. Sci. USA, 95: 5690-5693 (May 1998).
Kawano et al., Science, 278: 1696-1629 (1997).
Morita et al., J. Med. Chem., 38: 2176-2187 (1995).
Motoki et al., Biol. Pharm. Bull., 18(11): 1487-1491 (1995).
Schmieg et al., J. Exp. Med., 198(11): 1631-1641 (Dec. 1, 2003).
Taniguchi et al., Nature Immunology, 4(12): 1164-1165 (2003).
Tashiro et al., Tetrahedron Letters, 48: 3343-3347 (2007).
Watanabe et al. The Journal of Immunology, 155: 2972-2983 (1995).
Yang et al., Angew. Chem. Int. Ed., 43: 3818-3822 (2004).

* cited by examiner

*Primary Examiner* — Traviss C McIntosh, III
(74) *Attorney, Agent, or Firm* — Leydig, Voit & Mayer, Ltd.

(57) ABSTRACT

The invention provides a glycolipid effective for cancer treatment and the like and a synthetic intermediate therefor, as well as a medicament containing the glycolipid and the like. The glycolipid is represented by the formula (1) or a salt thereof

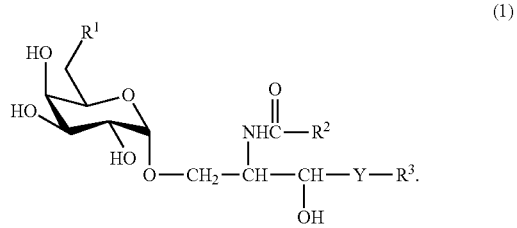

(1)

12 Claims, 9 Drawing Sheets

GLYCOLIPID AND USE THEREOF

TECHNICAL FIELD

The present invention relates to a novel glycolipid and use thereof.

BACKGROUND ART

Immune systems of living organisms have an elaborate surveillance function to distinguish normal cells and abnormal cells in the body of themselves, and remove only the abnormal cells. However, when the surveillance function collapses, abnormal cells produced by mutation and the like cannot be removed but proliferate in the body. A mass of such proliferated abnormal cells is a tumor, i.e., cancer.

Cancer is mainly treated by surgical removal of cancer or use of anti-cancer agents. However, these treatment methods place physical burden due to removal surgery or side effects of anti-cancer agents, as well as mental burden due to operative scar.

In such background, a treatment method using an immunotherapy in combination is drawing attention. In the immunotherapy, cancer cells are attacked by increasing the number of immunocytes in patients themselves, and activating them. If the size of tumor formed by cancer cells can be reduced, the physical burden due to the removal surgery becomes small. In addition, since the operative scar is small, the mental burden is drastically reduced.

Natural killer (NK) T cells are immunocytes belonging to a novel lymphocyte lineage showing characteristics different from those of other lymphocyte lineages (T, B, NK cells). Since cytotoxic perforin granules are present in NKT cells, they are analogous to NK cells (non-patent document 1). However, since NKT cells express not only NK cell marker but also T cell receptor (TCR), it is clear that they form a definitively different, new cell group (non-patent document 2). NKT cells can produce both Th-1 type cytokine (mainly interferon (IFN)-γ produced by helper T (Th)-1 cell that promotes immunostimulatory action and Th-2 type cytokine (mainly interleukin (IL)-4) produced by Th-2 cell that promotes immunosuppressive action (non-patent document 3), which suggests a possibility of controlling the balance of immune system (non-patent document 4). Therefore, by controlling the function of NKT cells, disrupted balance of the immune system is controlled and the surveillance function is enhanced, whereby cancer can be treated.

The most noticeable characteristic of NKT cells is that the α chain of TCR expressed by NKT cells is common to all members of one species. In other words, this means that all NKT cells of the living organisms belonging to the same species are activated by the same substance. This α chain is Vα24 in human and Vα14 in mouse, and they show extremely high homology between the two species. In addition, only very limited kinds of β chain are known to form a pair with the α chain. For this reason, this TCR is also called a "non-variable TCR".

There are various kinds of glycosphingolipids which are known to be present in the body. In glycosphingolipids in the body, various sugars generally form a β-bond with ceramide. While the existent amount thereof varies depending on the organ, they are present in the cellular membrane of various organs (non-patent document 5).

In the meantime, a report has recently been documented that glycosphingolipids wherein sugar forms an α-bond with ceramide has a strong immunostimulatory action and an antitumor activity. α-Galactosylceramide represented by Agelasphins is a glycolipid isolated from an extract of Agelas mauritianus, one kind of sponge, and is known to strongly activate NKT cells (non-patent document 6).

After intake by antigen presenting cell (APC), which is represented by dendritic cell (DC) and the like, α-galactosylceramide is presented on the cellular membrane by a CD1d protein similar to major histocompatible complex (MHC) class I molecule. NKT cells are activated by recognition using TCR of the thus-presented complex of CD1d protein and α-galactosylceramide, which triggers various immune reactions.

α-Galactosylceramide is glycosphingolipids wherein galactose is bonded by α-configuration to a ceramide formed by acylation of sphingosine base with long chain fatty acid. Various analogs have been synthesized heretofore, and the correlation between structures and activities thereof has been investigated. It has been clarified that, in a series of synthesis analogs, for example, α-galactosylceramide represented by the following formula (a) (hereinafter to be referred to as "α-GalCer") shows the strongest activity, and further, that the corresponding β-configuration (β-GalCer) does not show an immunostimulatory activity (non-patent document 7).

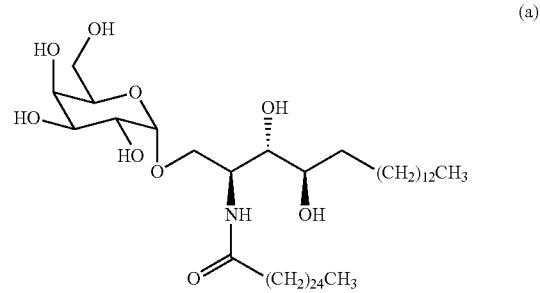

(a)

Taking note of such function of NKT cells, therapeutic drugs containing α-GalCer as an active ingredient have been proposed or developed in recent years. However, NKT cells activated by the administration of α-GalCer show an action to potentiate IFN-γ, which is a cytokine that induces immunostimulatory activity and is useful for cancer treatment, as well as IFN-γ production by NKT cells, and simultaneously produce, along with the production of IL-12, which is a cytokine produced by dendritic cells, IL-4, which is a cytokine that induces an immunosuppressive action, and IL-10, which is a cytokine that induces an immunity regulating action. As a result, problems occur since immunostimulatory activity is suppressed and a sufficient effect for cancer treatment is difficult to provide.

In recent years, a glycolipid (α-C-GalCer) that preferentially produces IFN-γ, which is a cytokine that induces an immunostimulatory action of NKT cell, has been developed (patent documents 1-3, non-patent document 8). α-C-GalCer is an analog wherein the oxygen atom forming a glucoside bond of α-GalCer is substituted by a methylene group. It has been reported that the in vivo stability is enhanced and the efficacy is maintained for a long time since, in α-C-GalCer, the bond between sugar and ceramide is converted from a glycoside bond to a carbon-carbon bond (non-patent document 9). However, α-C-GalCer is difficult for clinical application, since it shows only a very weak activity on human NKT cells in vitro.

On the other hand, of the present inventors, TASHIRO et al. independently found that a novel glycolipid having a carba-sugar represented by the formula:

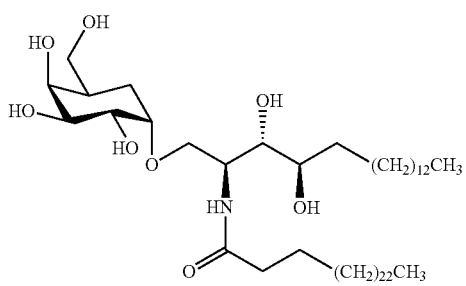

(to be referred to as "carba-glycolipid A" in the present specification) strongly induces IFN-γ production by NKT cells (non-patent document 10).

Since the compound also shows strong activity in the human (in vitro) system, clinical application is expected. However, since synthesis of the compound requires multiple steps, the development of a more convenient synthesis method, or a novel analog permitting easy preparation and having equivalent or higher activity has been desired.

As the glycolipid having fucosyl as a sugar moiety, (1) (2S,3R)-1-O-(6'-deoxy-α-D-galactopyranosyl)-2-(N-tetradecanoylamino)-1,3-octadecanediol represented by the following formula (b) (patent document 4, compound 12; non-patent documents 12, 13, AGL-571), formula:

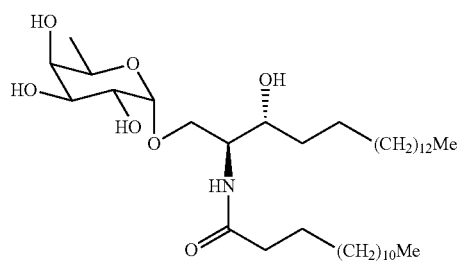

(2) (2S,3S,4R)-1-O-(6'-deoxy-α-D-galactopyranosyl)-2-(N-tetracosanoylamino)-1,3,4-octadecanetriol represented by the following formula (c) (patent document 5, DB03-8), formula:

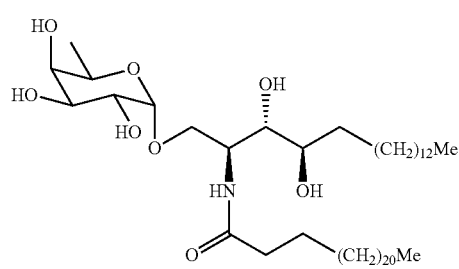

(3) (2S,3S,4R)-1-O-(α-L-fucopyranosyl)-2-(N-hexacosanoylamino)-1,3,4-octadecanetriol represented by the following formula (d) (non-patent document 11, compound 27), formula:

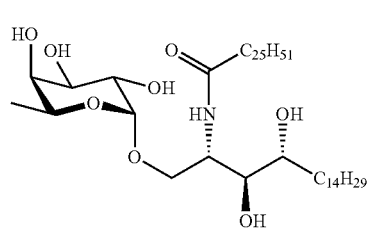

(4) (2S,3S,4R)-1-O-(β-L-fucopyranosyl)-2-(N-hexacosanoylamino)-1,3,4-octadecanetriol represented by the following formula (e) (non-patent document 11, compound 30), formula:

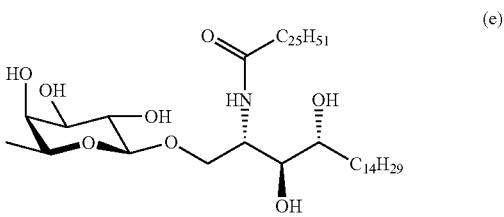

are disclosed.

patent document 1: US-A-2005/0222048
patent document 2: WO2003/105769
patent document 3: DE-A-10128250
patent document 4: WO1994/09020
patent document 5: US-A-publication 2007/0238673
non-patent document 1: Proc. Natl. Acad. Sci. USA 1998, 95, 5690-5693
non-patent document 2: J. Immunol. 1995, 155, 2972-2983
non-patent document 3: J. Immunol. 1998, 161, 3271-3281
non-patent document 4: Nat. Immunol. 2003, 4, 1164-1165
non-patent document 5: Biochim. Biophys. Acta 1973, 315-335
non-patent document 6: Science 1997, 278, 1626-1629
non-patent document 7: J. Med. Chem. 1995, 38, 2176-2187
non-patent document 8: Angew. Chem. Int. Ed. Engl. 2004, 43, 3818-3822
non-patent document 9: J. Exp. Med. 2003, 198, 1631-1641
non-patent document 10: Tetrahedron Lett. 2007, 48, 3343-3347
non-patent document 11: Tetrahedron 2005, 61, 1855-1862
non-patent document 12: Biol. Pharm. Bull. 1995, 18, 1487-1491
non-patent document 13: Bioorg. Med. Chem. 1998, 6, 1905-1910

DISCLOSURE OF THE INVENTION

Problems to be Solved by the Invention

The present invention has been made in view of such situation, and its problem to be solved is provision of a novel compound effective for cancer treatment and an intermediate useful for synthesizing the compound. The present invention also aims to provide a medicament such as an anti-cancer agent and the like containing the novel compound.

Means of Solving the Problems

The present inventors have conducted intensive studies in an attempt to solve the above-mentioned problems, and found that a compound represented by the following formula (1) selectively produces a particular cytokine. The present inventors have further studied in detail, and found that a specific immunostimulatory activity is expressed by the selective production of the particular cytokine, which is extremely effective for cancer treatment, which resulted in the completion of the present invention.

Accordingly, the present invention provides the following.

[1] A compound represented by the following formula (1)

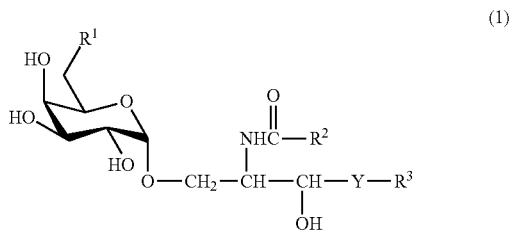

wherein $R^1$ is a hydrogen atom, an alkyl group having a carbon number of 1 to 7, an alkoxy group having a carbon number of 1 to 6 or a halogen atom, $R^2$ and $R^3$ are each independently a substituted or unsubstituted hydrocarbon group having a carbon number of 1 to 28, and Y is —$CH_2$—, —CH(OH)— or —CH=CH—, provided that when $R^1$ is a hydrogen atom, then $R^2$ is a substituted or unsubstituted hydrocarbon group having a carbon number of 24 to 28 (hereinafter to be referred to as "compound (1)"), or a salt thereof.

[2] The compound of the above-mentioned [1], wherein $R^1$ is a hydrogen atom, a methyl group, a methoxy group, an ethoxy group, an n-propyloxy group or a fluorine atom, or a salt thereof.

[3] The compound of the above-mentioned [1] or [2], wherein $R^1$ is an alkyl group having a carbon number of 1 to 7, an alkoxy group having a carbon number of 1 to 6 or a halogen atom and $R^2$ is a substituted or unsubstituted alkyl group having a carbon number of 1 to 28, or $R^1$ is a hydrogen atom and $R^2$ is a substituted or unsubstituted alkyl group having a carbon number of 24 to 28, or a salt thereof.

[4] The compound of any of the above-mentioned [1] to [3], wherein $R^3$ is a substituted or unsubstituted alkyl group having a carbon number of 1 to 28, or a salt thereof.

[5] The compound of any of the above-mentioned [1] to [4], wherein Y is —CH(OH)—, or a salt thereof.

[6] A compound represented by the following formula (2)

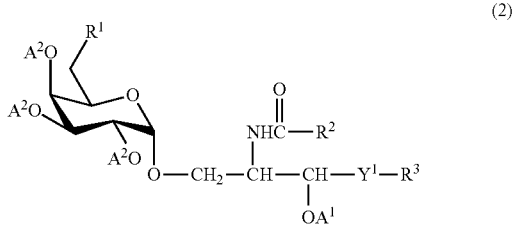

wherein $R^1$ is a hydrogen atom, an alkyl group having a carbon number of 1 to 7, an alkoxy group having a carbon number of 1 to 6 or a halogen atom, $R^2$ and $R^3$ are each independently a substituted or unsubstituted hydrocarbon group having a carbon number of 1 to 28, Y' is —$CH_2$—, —CH($OA^1$)- or —CH=CH—, $A^1$ is a hydrogen atom or a hydroxyl-protecting group, and $A^2$ is a hydroxyl-protecting group, provided that when $R^1$ is a hydrogen atom, then $R^2$ is a substituted or unsubstituted hydrocarbon group having a carbon number of 24 to 28 (hereinafter to be referred to as "compound (2)"), or a salt thereof.

[7] A medicament comprising compound (1) or a salt thereof.
[8] An immunostimulator comprising compound (1) or a salt thereof.
[9] A selective IFN-γ production inducer comprising compound (1) or a salt thereof.
[10] An anti-cancer agent comprising compound (1) or a salt thereof.
[11] A method for immunostimulation, comprising administering an effective amount of compound (1) or a salt thereof to a subject.
[12] A method for inducing selective IFN-γ production, comprising administering an effective amount of compound (1) or a salt thereof to a subject.
[13] A method for treating cancer, comprising administering an effective amount of compound (1) or a salt thereof to a subject.
[14] Use of compound (1) or a salt thereof for the production of an immunostimulator.
[15] Use of compound (1) or a salt thereof for the production of a selective IFN-γ production inducer.
[16] Use of compound (1) or a salt thereof for the production of an anti-cancer agent.

Effect of the Invention

The present inventors have conducted intensive studies in an attempt to solve the aforementioned problems and found that a compound wherein the 6-position hydroxyl group of sugar, which is a part of the general skeleton of galactosylceramide (one kind of glycolipid) has been converted to other functional group (an alkyl group having a carbon number of 1 to 7, an alkoxy group having a carbon number of 1 to 6, a halogen atom) or a hydrogen atom has a specific immunomodulating capacity, and is extremely effective for cancer treatment, which resulted in the completion of the present invention.

When compound (1) of the present invention forms a complex with the CD1d protein possessed by antigen presenting cell (APC) and the complex is presented to NKT cells, the NKT cells recognizes the complex via TCR, and can preferentially produce IFN-γ, which is one kind of cytokine that activates the function of immunocytes, in a large amount, from among the immunoregulatory functions it has.

Even a trace amount of compound (1) of the present invention strongly activates NKT cells, and produces IFN-γ in an amount larger than that by the compounds reported heretofore. Therefore, sufficient efficacy can be afforded by administration of a small amount of the compound.

Compound (1) and a salt thereof of the present invention are effective for the treatment of cancer and the like.

Compound (2) and a salt thereof of the present invention are useful as synthetic intermediates for compound (1) or a salt thereof.

BEST MODE FOR CARRYING OUT THE INVENTION

Figure 1:
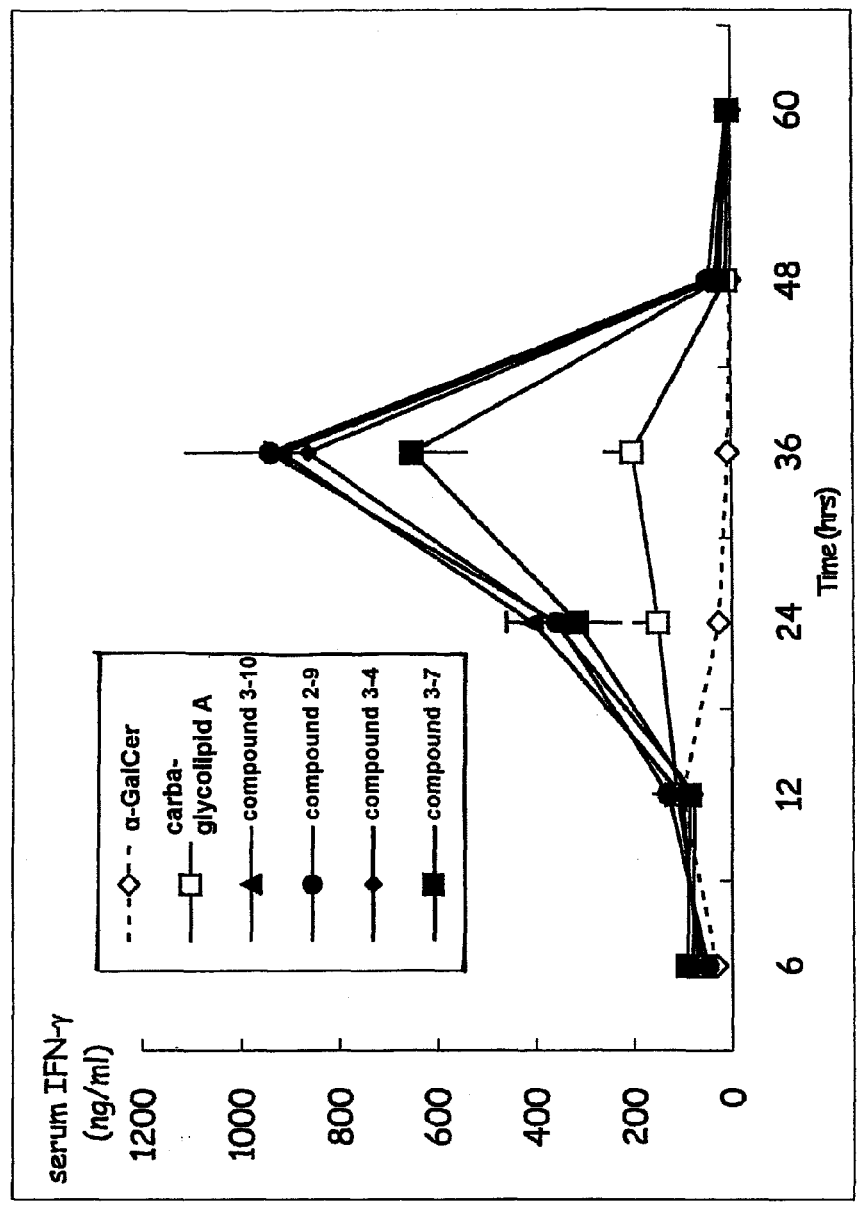
FIG. 1 shows the concentration of IFN-γ in the serum after lapse of indicated time from the administration of synthetic glycolipid to mouse in vivo.

The present invention is explained in detail in the following by referring to a preferable embodiment thereof.

First, the definitions of the symbols used in the formulas in the present specification are explained.

$R^1$ is a hydrogen atom, an alkyl group having a carbon number of 1 to 7, an alkoxy group having a carbon number of 1 to 6 or a halogen atom.

The alkyl group having a carbon number of 1 to 7 for $R^1$ is a substituted or unsubstituted alkyl group, and may form a ring. For example, methyl, ethyl, n-propyl, isopropyl, cyclopropyl, cyclopropylmethyl, n-butyl, isobutyl, sec-butyl, tert-butyl, pentyl, hexyl, heptyl, cyclohexylmethyl and the like can be mentioned, with preference given to methyl and ethyl.

The alkoxy group having a carbon number of 1 to 6 for $R^1$ is an oxygen atom bound with a substituted or unsubstituted alkyl group, wherein the alkyl moiety thereof may form a ring. For example, methoxy, ethoxy, n-propyloxy, isopropyloxy, cyclopropyloxy, cyclopropylmethyloxy, n-butoxy, isobutyloxy, sec-butyloxy, tert-butyloxy, pentyloxy, hexyloxy, cyclohexyloxy and the like can be mentioned, with preference given to methoxy, ethoxy and n-propyloxy.

Examples of the halogen atom for $R^1$ include a fluorine atom, a chlorine atom, a bromine atom and an iodine atom, with preference given to a fluorine atom and a chlorine atom.

$R^2$ and $R^3$ are each independently a substituted or unsubstituted hydrocarbon group having a carbon number of 1 to 28. In the present specification, the "hydrocarbon group" is a concept encompassing a substituted or unsubstituted alkyl group having a carbon number of 1 to 28, a substituted or unsubstituted alkenyl group having a carbon number of 2 to 28, a substituted or unsubstituted alkynyl group having a carbon number of 2 to 28, a substituted or unsubstituted cycloalkyl group having a carbon number of 3 to 28, a substituted or unsubstituted cycloalkenyl group having a carbon number of 3 to 28, and a substituted or unsubstituted aryl group having a carbon number of 6 to 14, which may be in any of linear form, branched form and cyclic form, may be a saturated hydrocarbon group or an unsaturated hydrocarbon group, and may have an unsaturated bond either in a molecule or at the terminal. Among these, as $R^2$ and $R^3$, a substituted or unsubstituted alkyl group having a carbon number of 1 to 28 is preferable.

When $R^1$ is a hydrogen atom, $R^2$ is a substituted or unsubstituted hydrocarbon group having a carbon number of 24 to 28, and a substituted or unsubstituted alkyl group having a carbon number of 24 to 28 is preferable.

Examples of the substituent of the hydrocarbon group for $R^2$ or $R^3$ include a halogen atom (preferably chlorine atom, fluorine atom); an alkoxy group (preferably $C_{1-24}$, more preferably $C_{1-16}$, still more preferably $C_{1-10}$, particularly preferably $C_{1-4}$) such as a methoxy group, an ethoxy group, a propoxy group, an isopropoxy group, a butoxy group, a tert-butoxy group and the like; an aryloxy group (preferably $C_{6-14}$) such as a phenoxy group and the like; a hydroxyl group; an amino group; an alkylamino group such as a methylamino group, a dimethylamino group, an ethylamino group, a diethylamino group and the like; a cycloalkylamino group; an alkylcarbonylamino group such as an acetamide group and the like; a cycloalkylcarbonylamino group; an electron-donating group [arylcarbonylamino group such as benzoylamino group and the like (preferably, an arylcarbonylamino group wherein the aryl moiety is an aryl group having a carbon number of 6-14) and the like], further, a carboxyl group; an alkoxycarbonyl group; an acyl group (acyl group is as mentioned below, preferably an alkyl-carbonyl group wherein the alkyl moiety is a straight chain or branched alkyl group having a carbon number of 1 to 24); a carbamoyl group; an electron-withdrawing group such as a trifluoromethyl group and the like.

The "acyl group" in the present specification is, for example, a formyl group; an alkyl-carbonyl group (e.g., an alkyl-carbonyl group wherein the alkyl moiety is a straight chain or branched alkyl group having a carbon number of 1 to 24 (preferably 1 to 12) (e.g., acetyl group, propionyl group, butyryl group, isobutyryl group, valeryl group, pivaloyl group, hexanoyl group)); a cycloalkyl-carbonyl group (e.g., a cycloalkyl-carbonyl group wherein the cycloalkyl moiety is a cycloalkyl group having a carbon number of 3 to 10); an alkenyl-carbonyl group (e.g., an alkenyl-carbonyl group wherein the alkenyl moiety is a straight chain or branched alkenyl group having a carbon number of 2 to 12 (e.g., acryloyl group, methacryloyl group)); an aryl-carbonyl group (e.g., an aryl-carbonyl group wherein the aryl moiety is an aryl group having a carbon number of 6 to 14 (e.g., benzoyl group, naphthoyl group)) and the like. The aryl group of the aryl-carbonyl group is, for example, a monocyclic-tricyclic aromatic hydrocarbon group, and specific examples include a phenyl group, a naphthyl group, an anthryl group and a phenanthryl group. Of these, as the acyl group, a formyl group, an acetyl group, a propionyl group, a butyryl group, an isobutyryl group, a benzoyl group, a naphthoyl group and the like are preferable, and an acetyl group and a benzoyl group are more preferable.

Examples of the alkyl moiety of the above-mentioned alkylamino group and alkylcarbonylamino group include a straight chain or branched alkyl group (preferable carbon number 1-24, more preferable carbon number 1-16, still more preferable carbon number 1-10, particularly preferable carbon number 1-4) such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group and the like.

examples of the cycloalkyl moiety of the above-mentioned cycloalkylamino group and cycloalkylcarbonylamino group include a cycloalkyl group (preferable carbon number 3-24, more preferable carbon number 3-16, still more preferable carbon number 3-10, particularly preferable carbon number 3-6) such as a cyclopentyl group, a cyclohexyl group and the like.

Examples of the alkoxy moiety of the above-mentioned alkoxycarbonyl group include those similar to the above-mentioned alkoxy group.

The above-mentioned substituents may be further substituted at substitutable position(s) by at least one kind from halogen, an alkyl group, a cycloalkyl group, an alkenyl group, an alkynyl group, a phenyl group, an alkoxy group, a hydroxyl group, an amino group, an alkylamino group and a cycloalkylamino group.

Examples of the halogen, alkoxy group, alkylamino group and cycloalkylamino group include those similar to the above.

Examples of the alkyl group include an alkyl group (preferable carbon number 1-24, more preferable carbon number 1-16, still more preferable carbon number 1-10, particularly preferable carbon number 1-4) such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group and the like.

Examples of the cycloalkyl group include a cycloalkyl group (preferable carbon number 3-24, more preferable carbon number 3-16, still more preferable carbon number 3-10, particularly preferable carbon number 3-6) such as a cyclopentyl group, a cyclohexyl group and the like.

Examples of the alkenyl group include an alkenyl group (preferable carbon number 2-24, more preferable carbon number 2-16, still more preferable carbon number 2-10, particularly preferable carbon number 2-4) such as a vinyl group, a propenyl group, a butenyl group and the like.

Examples of the alkynyl group include an alkynyl group (preferable carbon number 2-24, more preferable carbon number 2-16, still more preferable carbon number 2-10, particularly preferable carbon number 2-4) such as an ethynyl group, a propargyl group, a butynyl group, a pentynyl group and the like.

Of these, as $R^2$, a substituted or unsubstituted alkyl group is preferable, and a linear alkyl group is preferable. When $R^1$ is an alkyl group having a carbon number of 1 to 7, an alkoxy group having a carbon number of 1 to 6 or a halogen atom, the carbon number of $R^2$ is preferably 18-26, more preferably 24 to 26. When $R^1$ is a hydrogen atom, the carbon number of $R^2$ is preferably 24 to 26. Specific examples of $R^2$ include —$(CH_2)_{23}$—$CH_3$, —$(CH_2)_{24}$—$CH_3$, —$(CH_2)_{25}$—$CH_3$ and the like.

In addition, as $R^3$, a substituted or unsubstituted alkyl group is preferable, and a linear alkyl group is preferable. The carbon number of $R^3$ is preferably 9-20, more preferably 12-18. Specific examples of $R^3$ include —$(CH_2)_{11}$—$CH_3$, —$(CH_2)_{12}$—$CH_3$, —$(CH_2)_{13}$—$CH_3$, —$(CH_2)_{14}$—$CH_3$, —$(CH_2)_{15}$—$CH_3$, —$(CH_2)_{16}CH_3$, —$(CH_2)_{17}$—$CH_3$ and the like.

Y is —$CH_2$—, —CH(OH)— or —CH=CH—. Of these, —CH(OH)— is preferable.

$Y^1$ is —$CH_2$—, —CH($OA^1$)- or —CH=CH—. Of these, —CH($OA^1$)- is preferable. $A^1$ is as mentioned below.

$A^1$ is a hydrogen atom or a hydroxyl-protecting group. Examples of the hydroxyl-protecting include an acyl group, a t-butyldimethylsilyl (TBS) group, a benzyl (Bn) group, a p-methoxybenzyl (PMB) group and the like. The acyl group is as mentioned above. Of these, a TBS group and a Bn group are preferable.

When $Y^1$ is —CH($OA^1$)-, two $A^1$ may be the same or different; however, they are preferably the same.

When $Y^1$ is —CH($OA^1$)-, two $A^1$ in combination may form a protecting group for diol. Examples of the diol-protecting group include a group represented by

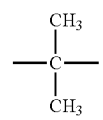

(that is, a group that protects diol and forms acetonide) and the like.

Examples of the hydroxyl-protecting group for $A^2$ include an acyl group, a TBS group, a trimethylsilyl (TMS) group, a Bn group, a PMB group and the like. The acyl group is as mentioned above. Of these, a Bn group and a PMB group are preferable.

In the present invention, the α configuration is employed from among the stereoisomers derived from the cyclic structure of sugar. The present inventors have found that the β configuration shows extremely lower cytokine-producing ability.

When compound (1) and compound (2) have stereoisomers, any isomers are also encompassed in the present invention, which may be a mixture (including racemate) of two or more kinds of isomers at any ratio.

Particularly, compound (1) contains an optical isomer derived from asymmetric carbon in the lipid moiety. In the present invention, they may be a single optically active form or a mixture (including racemate) of two or more kinds of optically active forms at any ratio. The asymmetric carbon to be bonded to —$NHCOR^2$ is preferably an S configuration. The asymmetric carbon having —OH and adjacent to the asymmetric carbon to be bonded to —$NHCOR^2$ is preferably an anti configuration relative to the asymmetric carbon to be bonded to —$NHCOR^2$. When Y is —CH(OH)—, the asymmetric carbon in —CH(OH)— for Y is preferably an R configuration.

In addition, compound (2) contains an optical isomer derived from asymmetric carbon in the lipid moiety. In the present invention, it may be a single optically active form or a mixture (including racemate) of two or more kinds of optically active forms at any ratio. The asymmetric carbon to be bonded to —$NHCOR^2$ is preferably an S configuration. The asymmetric carbon having —$OA^1$ and adjacent to the asymmetric carbon to be bonded to —$NHCOR^2$ is preferably an anti configuration relative to the asymmetric carbon to be bonded to —$NHCOR^2$. When $Y^1$ is —CH($OA^1$)-, the asymmetric carbon in —CH($OA^1$)- for $Y^1$ is preferably an R configuration.

Examples of the lipid moiety of compound (1) include

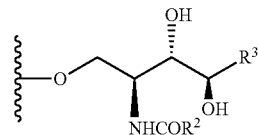

wherein each symbol is as defined above, and the like.

Examples of the lipid moiety of compound (2) include

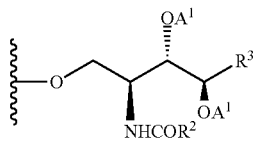

wherein each symbol is as defined above, and the like.

The salts of compound (1) and compound (2) are preferably pharmacologically acceptable salts. Examples thereof include inorganic acid salts such as hydrochloride, hydrobromide, hydroiodide, sulfate, nitrate, phosphate and the like; organic acid salts such as succinate, fumarate, acetate, methanesulfonate, toluenesulfonate and the like; alkali metal salts such as sodium salt, potassium salt and the like; alkaline earth metal salts such as magnesium salt, calcium salt and the like; ammonium salts such as ammonium salt, alkylammonium salt and the like, and the like.

Specific preferable examples of compound (1) in the present invention are shown in, but are not limited to, Table 1.

TABLE 1

(1)

| Compound No. | $R^1$ | $R^2$ | Y | $R^3$ |
|---|---|---|---|---|
| 2-9' | —OCH$_3$ | —(CH$_2$)$_{24}$CH$_3$ | —CH(OH)— | —(CH$_2$)$_{13}$CH$_3$ |
| 3-4' | —CH$_3$ | —(CH$_2$)$_{24}$CH$_3$ | —CH(OH)— | —(CH$_2$)$_{13}$CH$_3$ |
| 3-7' | —F | —(CH$_2$)$_{24}$CH$_3$ | —CH(OH)— | —(CH$_2$)$_{13}$CH$_3$ |
| 3-10' | —H | —(CH$_2$)$_{24}$CH$_3$ | —CH(OH)— | —(CH$_2$)$_{13}$CH$_3$ |
| 3-13' | —OC$_2$H$_5$ | —(CH$_2$)$_{24}$CH$_3$ | —CH(OH)— | —(CH$_2$)$_{13}$CH$_3$ |
| 3-16' | —O(CH$_2$)$_2$CH$_3$ | —(CH$_2$)$_{24}$CH$_3$ | —CH(OH)— | —(CH$_2$)$_{13}$CH$_3$ |

Specific examples of preferable compound (1) in the present invention include, but are not limited to, compound 2-9, compound 3-4, compound 3-7, compound 3-10, compound 3-13 and compound 3-16 described in Examples.

Specific examples of preferable compound (2) in the present invention include, but are not limited to, compound 2-7 and compound 2-8 described in Examples.

Now, preferable embodiments of the production methods of compounds (1) and (2) of the present invention are explained. The compounds of the present invention can be produced by various methods known per se for those of ordinary skill in the art and, for example, compound (1) and (2) can be produced according to the method described in the following Scheme or a method analogous thereto.

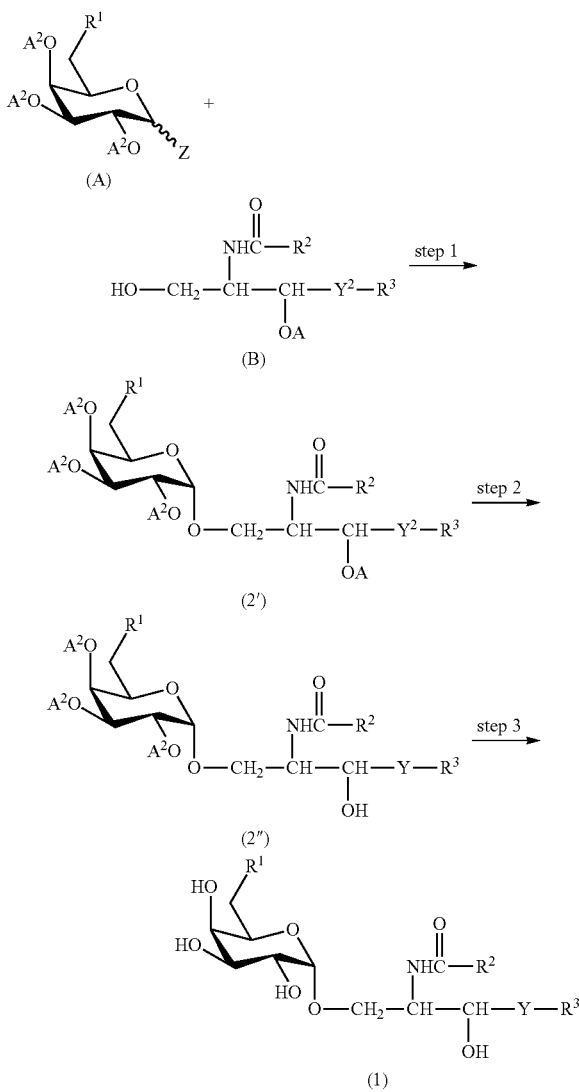

In the Scheme, Z is a halogen atom (e.g., fluorine atom), $Y^2$ is —CH$_2$—, —CH(OA)- or —CH=CH—, A is a hydroxyl-protecting group, and other symbols are as defined above. Examples of the hydroxyl-protecting group for A include those similar to the hydroxyl-protecting group for the aforementioned $A^1$. The compound (2') and compound (2") are encompassed in compound (2) of the present invention.

Starting material compound (A) can be prepared as shown below, using, as a starting material, compound 2-2' produced by, for example, the method described in T. J. Lucas et al., Carbohydr. Res., 1975, 39, 39-45 or a method analogous thereto.

(i) Compound (A) wherein $R^1$ is an alkoxy group having a carbon number of 1 to 6 (compound 2-5')

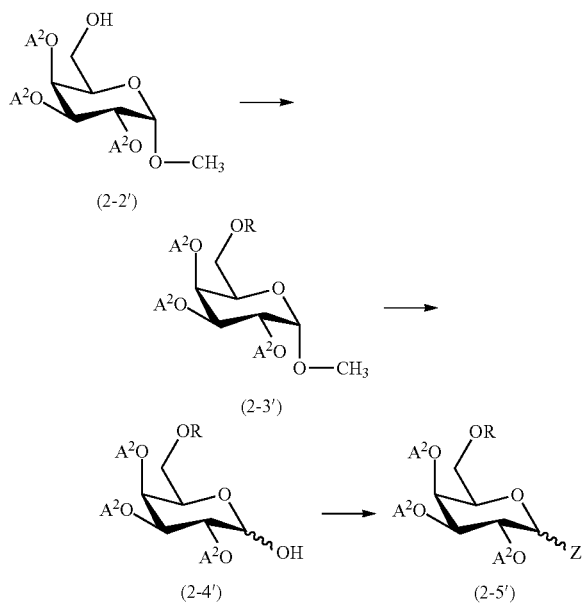

wherein R is alkyl having a carbon number of 1 to 6 (e.g., methyl, ethyl, n-propyl), and other symbols are as defined above.

Compound 2-3' can be obtained by reacting compound 2-2' with alkyl halide in the presence of a base. Examples of the base include sodium hydride, n-butyllithium and the like. The amount of the base to be used is generally 1-3 equivalents relative to compound 2-2'. Examples of the alkyl halide include methyl iodide, ethyl iodide, propyl bromide and the like. The amount of the alkyl halide to be used is generally 1-3 equivalents relative to compound 2-2'.

Examples of the solvent include aprotic solvents such as N,N-dimethylformamide, ethers (e.g., diethyl ether, tetrahydrofuran) and the like, and a mixed solvent thereof. The amount of the solvent to be used is generally 10- to 20-fold volume relative to compound 2-2'.

The reaction temperature is generally 0 to 80° C., and the reaction time is generally 1-24 hr.

Compound 2-3' can be isolated by a conventional method. For example, compound 2-3' can be isolated by adding water to the reaction mixture, extracting the mixture with ethyl acetate, washing the organic layer with water and saturated brine, drying the layer over anhydrous magnesium sulfate, and filtering and concentrating the layer.

Compound 2-4' can be obtained by directly reacting compound 2-3' with an acid. Alternatively, compound 2-4' can be obtained by leading compound 2-3' to the corresponding O-acetyl form and alcoholyzing the form.

When O-acetyl form is used, for example, O-acetyl form is prepared by a treatment with a catalytic amount of an acid in acetic anhydride, and alcoholyzing the form. Examples of the acid include concentrated sulfuric acid, concentrated hydrochloric acid, p-toluenesulfonic acid and the like. The amount of the acetic anhydride to be used is generally 5- to 20-fold volume relative to compound 2-3'. The reaction temperature is generally 0° C. to room temperature, and the reaction time is generally 5 min-1 hr. After neutralization, O-acetyl form can be obtained by concentration under reduced pressure.

The obtained O-acetyl form can be alcoholyzed by a treatment with a base such as sodium methoxide, sodium hydroxide and the like in a solvent such as alcohol solvent (e.g., methanol, ethanol and the like).

Compound 2-4' can be isolated by a conventional method and, for example, may be acidified with a cation exchange resin, and purified by filtration and concentration.

Compound 2-5' can be obtained by reacting compound 2-4' with a halogenating agent.

Examples of the halogenating agent include diethylaminosulfurtrifluoride, tris(dimethylamino)sulfoniumdifluorotrimethylsilicate and the like. The amount of the halogenating agent to be used is generally 1-3 equivalents relative to compound 2-4'.

Examples of the solvent include dichloromethane and the like. The amount of the solvent to be used is generally 10- to 30-fold volume relative to compound 2-4'.

The reaction temperature is generally −78° C. to room temperature, and the reaction time is generally 30 min-1 hr.

Compound 2-5' can be isolated by a conventional method. For example, compound 2-5' can be isolated by adding methanol to the reaction mixture, concentrating, diluting the residue with ethyl acetate, washing the organic layer with saturated aqueous sodium hydrogen carbonate solution, water and saturated brine, drying the layer over anhydrous magnesium sulfate, and filtering and concentrating the layer.

(ii) Compound (A) wherein $R^1$ is an alkyl group having a carbon number of 1 to 7 (compound 3-3' etc.)

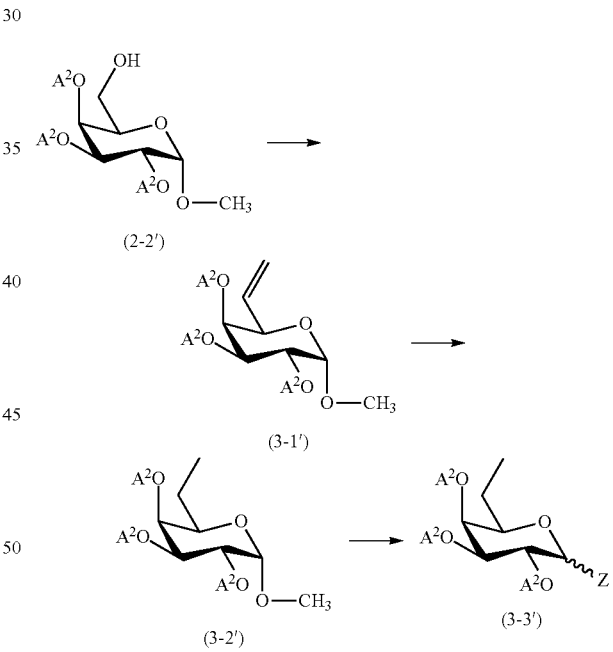

wherein each symbol is as defined above.

Compound 3-2' can be obtained by reacting compound 3-1' produced by the method described in K. Tatsuta et al. Carbohydr. Res., 1991, 222, 189-203, or a method analogous thereto, with hydrazine monohydrate and aqueous hydrogen peroxide. The amount of the hydrazine monohydrate to be used is generally 5-20 equivalents relative to compound 3-1'. The amount of the aqueous hydrogen peroxide to be used is generally 5-20 equivalents relative to compound 3-1'.

Examples of the solvent include ethanol and the like. The amount of the solvent to be used is generally 10- to 50-fold volume relative to compound 3-1'.

The reaction temperature is generally room temperature to 80° C., and the reaction time is generally 1-20 hr.

Compound 3-2' can be isolated by a conventional method. For example, compound 3-2' can be isolated by adding saturated sodium thiosulfate to the reaction mixture, diluting the mixture with ethyl acetate, washing the organic layer with water, saturated aqueous sodium thiosulfate solution and saturated brine, drying the layer over anhydrous magnesium sulfate, and filtering and concentrating the layer.

Conversion of compound 3-2' to compound 3-3' can be performed in the same manner as in conversion of compound 2-3' to compound 2-5'.

A compound wherein $R^1$ is other than methyl can be synthesized by selecting a Wittig reagent for the Wittig reaction following the Swern oxidation in the conversion of compound 2-2' to compound 3-1' in the aforementioned report of Tatsuta et al. In this case, compound 3-1' can be expressed as follows. $B^1$ and $B^2$ are each a substituted or unsubstituted alkyl group, and $B^1$ and $B^2$ may form a ring. In the formula, other symbols are as defined above.

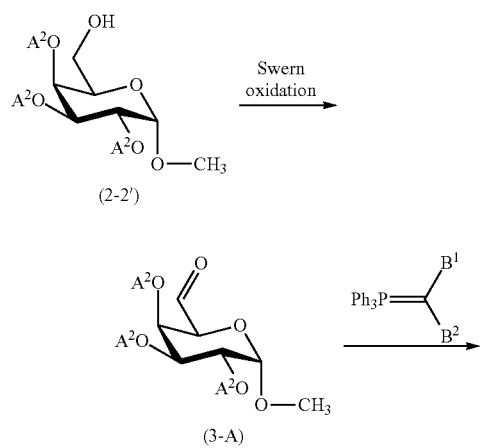

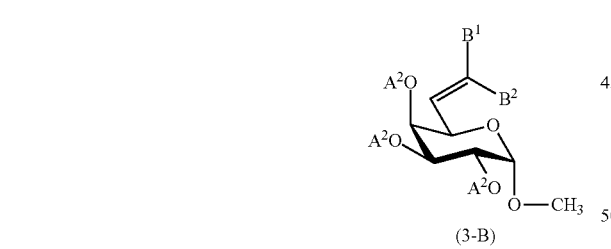

(iii) Compound (A) wherein $R^1$ is a halogen atom (compound 3-6')

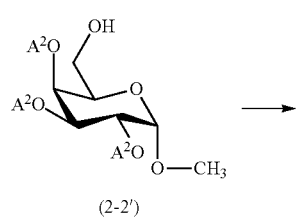

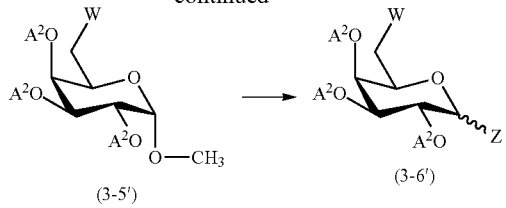

wherein W is a halogen atom (e.g., fluorine atom), and other symbols are as defined above.

Compound 3-5' can be obtained by reacting compound 2-2' with a halogenating agent in the presence of a base.

Examples of the base include triethylamine, pyridine and the like. The amount of the base to be used is generally 1-5 equivalents relative to compound 2-2'. Examples of the halogenating agent include diethylamino sulfur trifluoride, tris(dimethylamino)sulfonium difluorotrimethylsilicate and the like. The amount of the halogenating agent to be used is generally 1-3 equivalents relative to compound 2-2'.

Examples of the solvent include dichloromethane and the like. The amount of the solvent to be used is generally 10- to 30-fold volume relative to compound 2-2'.

The reaction temperature is generally −78° C. to room temperature, and the reaction time is generally 30 min-2 hr.

Compound 3-5' can be isolated by a conventional method. For example, compound 3-5' can be isolated by adding methanol to the reaction mixture, diluting the mixture with ethyl acetate, washing the organic layer with water, saturated aqueous sodium hydrogen carbonate solution and saturated brine, drying the layer over anhydrous magnesium sulfate, and filtering and concentrating the layer.

Conversion of compound 3-5' to compound 3-6' can be performed in the same manner as in conversion of compound 2-3' to compound 2-5'.

(iv) Compound (A) wherein $R^1$ is a hydrogen atom (compound 3-9')

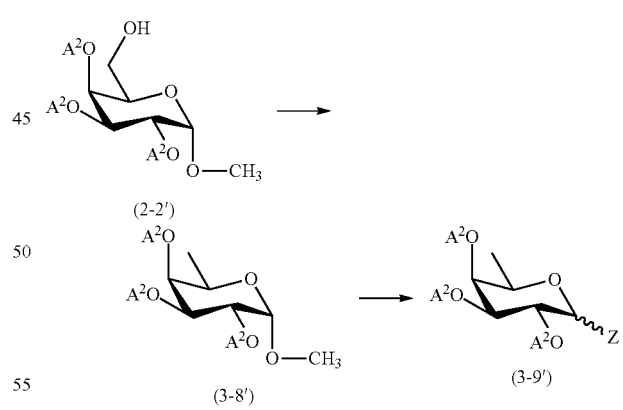

wherein each symbol is as defined above.

Compound 3-9' can be produced by subjecting compound 3-8' produced from compound 2-2' to the method described in S. Koto et al. Bull. Chem. Soc. Jpn., 2000, 73, 967-976, or a method analogous thereto, in the same manner as in conversion of compound 2-3' to compound 2-5'.

Starting material compound (B) can be prepared according to, for example, the method described in H. Takikawa et al. Tetrahedron, 1998, 54, 3141-3150 or S. Kim et al. Synthesis, 2004, 847-850 or a method analogous thereto.

(Step 1)

In step 1, compound (2') is obtained by reacting compound (A) with compound (B) in the presence of molecular sieves, tin chloride (II), and silver perchlorate.

The amount of compound (A) to be used is generally 1-3 equivalents relative to compound (B).

The amount of the molecular sieves to be used is generally 2- to 10-fold weight relative to compound (B). The amount of tin chloride (II) to be used is generally 1.5-3 equivalents relative to compound (A). The amount of the silver perchlorate to be used is generally 1.5-3 equivalents relative to compound (A).

Examples of the solvent include aprotic solvents such as acetonitrile, ether (e.g., diethyl ether, tetrahydrofuran) and the like. The amount of the solvent to be used is generally 5- to 20-fold volume relative to compound (A).

The reaction temperature is generally −18 to 20° C., and the reaction time is generally 1-2 hr.

Compound (2') can be isolated by a conventional method. For example, compound (2') can be isolated by adding diethyl ether to the reaction mixture, filtering the mixture, washing the filtrate with water and saturated brine, drying the filtrate over anhydrous magnesium sulfate, and filtering and concentrating the filtrate.

(Step 2)

In step 2, compound (2") is obtained by removing protecting group A from —OA of compound (2'). The removal method is determined by the kind of the protecting group and, for example, compound (2') and quaternary ammonium fluoride (e.g., tetra-n-butylammonium fluoride) are reacted in a solvent.

The amount of the quaternary ammonium fluoride to be used is generally 1-3 equivalents relative to compound (2').

The reaction temperature is generally 0° C. to room temperature, and the reaction time is generally 1-20 hr.

Examples of the solvent include aprotic solvents such as N,N-dimethylformamide, ethers (e.g., diethyl ether, tetrahydrofuran) and the like. The amount of the solvent to be used is generally 10- to 50-fold volume relative to compound (2').

Compound (2") can be isolated by a conventional method. For example, compound (2") can be isolated by adding water to the reaction mixture, extracting the mixture with ethyl acetate, washing the organic layer with water and saturated brine, drying the layer over anhydrous magnesium sulfate, and filtering and concentrating the layer.

(Step 3)

In step 3, compound (1) is obtained by removing the hydroxyl-protecting group from the sugar moiety in compound (2"). In this step, for example, compound (2") is reacted under a hydrogen atmosphere in the presence of a reduction catalyst in a solvent.

Examples of the reduction catalyst include palladium-C, palladium hydroxide, palladium hydroxide-activated carbon, platinum oxide, Raney-nickel and the like. The amount of the reduction catalyst to be used only needs to be a catalytic amount relative to compound (2").

Examples of the solvent include lower alcohols (e.g., methanol, ethanol), halogenated hydrocarbons (e.g., dichloromethane, chloroform) and ethers (e.g., diethyl ether, tetrahydrofuran), which may be used in a mixture. The amount of the solvent to be used is generally 20- to 200-fold volume relative to compound (2").

The reaction temperature is generally room temperature to 50° C., and the reaction time is generally 5-20 hr.

After completion of the reaction, compound (1) can be obtained by filtering and concentrating the reaction mixture.

Compound (1) and compound (2) of the present invention obtained as mentioned above can be converted to an object salt by a method known per se or a method analogous thereto.

Next, the pharmaceutical use of the present invention is explained.

By administration of compound (1) or a salt thereof of the present invention, a complex with the CD1d protein possessed by APC is formed, and the complex is presented to NKT cells. The NKT cells recognizes the complex via TCR, and can selectively produce IFN-γ, which is one kind of cytokine that activates the function of immunocytes, in a large amount, from among the immunoregulatory functions it has, while inhibiting the production of IL-4. In addition, compound (1) or a salt thereof of the present invention induces production of IL-12 having an action to enhance IFN-γ production by NKT cells. To be specific, the IFN-γ/IL-4 ratio was not less than 10 relative to 2 of α-GalCer, and extremely high selective IFN-γ production was confirmed as compared to conventionally known glycolipids (see Experimental Example 1). Therefore, compound (1) or a salt thereof of the present invention is useful as an anti-cancer agent or an immunostimulator for inhibiting tumor growth, and further for the treatment of a cell proliferation disorder or for correction of Th1/Th2 immunity balance.

Examples of the cancer treatment target include, but are not limited to, carcinomas of esophagus, stomach, liver, pancreas, breast, colon, kidney, lung (including small cell lung cancer, non-small cell lung cancer), gall bladder, ovary, testis, bladder, cervical division, thyroid gland, prostate and skin (including squamous cell cancer); hematopoietic neoplasm of the lymphoid system (including leukemia, acute lymphatic leukemia, acute lymphoblastic leukemia, B cell lymphoma, T cell lymphoma, Hodgkin lymphoma, non-Hodgkin lymphoma, hairy cell lymphoma, Burkitt's lymphoma); hematopoietic neoplasm of the myeloid system (including acute and chronic myeloid leukemia, myelodysplastic syndrome and acute promyeloid leukemia); tumors of mesenchymal origin (including fibrosarcoma and rhabdomyosarcoma); tumor in the central nervous system and the peripheral nervous system (including astrocytoma, neuroblastoma, glioma and schwannoma); other tumors (including melanoma, seminoma, teratocarcinoma, osteosarcoma, xeroderma pigmentosum, keratoacanthoma, follicular cancer of the thyroid, Kaposi's sarcoma).

The cell proliferation disorder is a concept including familial adenomatous polyposis, psoriasis, benign prostatic hyperplasia, neurofibromatosis, vascular smooth cell proliferation relating to atherosclerosis, pulmonary fibrosis, arthritis, glomerulonephritis, postoperative stenosis and restenosis.

As the subject of administration of compound (1) or a salt thereof of the present invention, mammals such as human and the like, and the like can be mentioned.

When compound (1) or a salt thereof of the present invention is administered to human, it can be safely administered orally or parenterally as it is or in the form of a pharmaceutical composition such as an agent for oral administration (e.g., powder, granule, tablet, capsule), an agent for parenteral administration (e.g., injection, suppository (e.g., rectal suppository, vaginal suppository)) and the like, which is obtained by mixing compound (1) or a salt thereof with a pharmacologically acceptable carrier (e.g., excipient, diluent) and the like. These preparations can be produced by a conventionally known method.

Examples of the injection include subcutaneous injection, intravenous injection, intramuscular injection, intraperitoneal injection, drip infusion and the like. Injections can also be prepared into an aqueous injection using compound (1) or a salt thereof together with a solubilizer (e.g., β-cyclodextrins), dispersing agent (e.g., carboxymethylcellulose, sodium alginate), preservative (e.g., methylparaben, propylparaben, benzyl alcohol, chlorobutanol), isotonicity agent (e.g., sodium chloride, glycerol, sorbitol, glucose) and the like according to a conventional method. It is also possible to prepare an oily injection by dissolving, suspending or emulsifying in vegetable oil (e.g., olive oil, sesame oil, peanut oil, cottonseed oil, corn oil), propylene glycol and the like.

An agent for oral administration can also be produced by appropriately adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose), lubricant (e.g., talc, magnesium stearate, polyethylene glycol) and the like to compound (1) or a salt thereof, compression molding the mixture, and coating the resulting product with hydroxypropylmethylcellulose and the like as necessary. Suppository can be produced by mixing compound (1) or a salt thereof and nonirritating excipient (e.g., polyethylene glycol, glyceride of higher fatty acid).

While the daily dose of compound (1) or a salt thereof varies depending on the age, body weight, symptom, dosage form, administration method, dosing period and the like, it is, for example, generally 0.1-1 mg/kg body weight, preferably 0.5-1 mg/kg body weight, more preferably 0.8-1 mg/kg body weight, per patient (adult, body weight about 60 kg), which can be orally or parenterally administered in one to several portions a day.

EXAMPLES

The present invention is explained in more detail in the following by referring to Examples, which are not to be construed as limitative.

Example 1

Synthesis of Compound 2-9

Compound 2-9 was synthesized according to the following scheme.

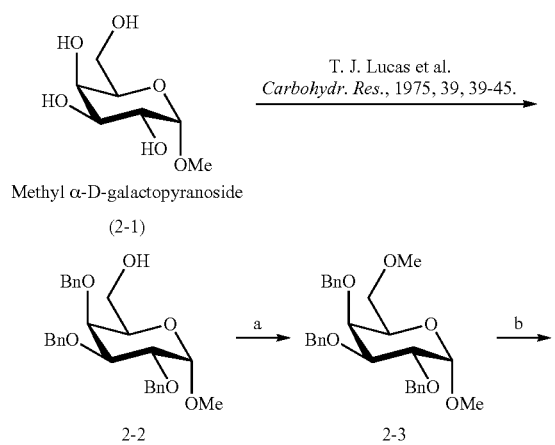

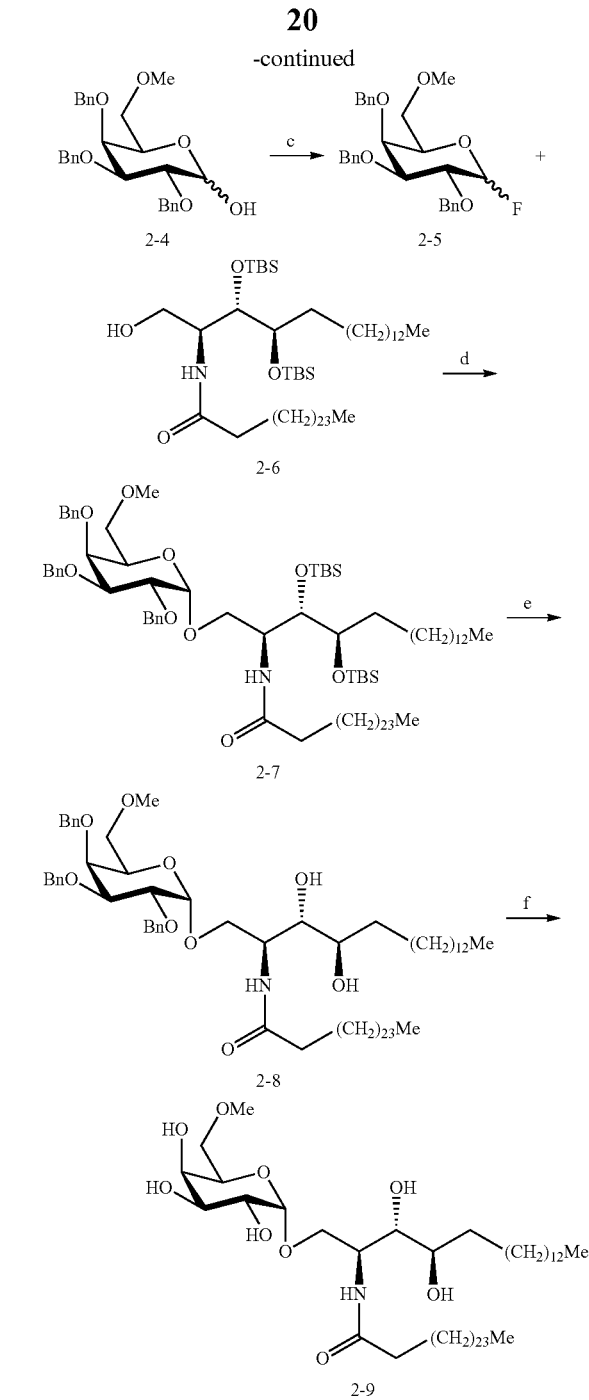

(Step a) Synthesis of Compound 2-3

To a solution of compound 2-2 (1.04 g, 2.24 mmol) known in the reference (T. J. Lucas et al., Carbohydr. Res., 1975, 39, 39-45) in N,N-dimethylformamide-tetrahydrofuran (1:1, 20 mL) was added sodium hydride (60% mineral oil suspension, 187 mg, 4.68 mmol) under ice-cooling. After stirring for 15 min under ice-cooling, methyl iodide (280 μL, 4.50 mmol) was added, and the mixture was stirred at room temperature for 16 hr. Water was added, and the mixture was extracted with ethyl acetate. The organic layer was washed successively with water and saturated brine, and dried over anhydrous magnesium sulfate. After filtration, the solvent was evaporated by concentration under reduced pressure, and the residue was purified by silica gel column chromatography (30 g, hexane-ethyl acetate=8:1) to give compound 2-3 (839 mg, 78%) as a colorless oil.

$n_D^{22}$=1.5172.

IR (film): $v_{max}$=1600 (w, arom.), 1500 (m, arom.), 1100 (br.s, C—O), 1050 (br.s, C—O), 740 (s), 700 (s) cm$^{-1}$.

$^1$H NMR (400 MHz, CDCl$_3$): δ=7.42-7.26 (15H, m), 4.96 (1H, d, J=12 Hz), 4.86 (1H, d, J=12 Hz), 4.84 (1H, d, J=12 Hz), 4.74 (1H, d, J=12 Hz), 4.692 (1H, d, J=12 Hz), 4.687 (1H, d, J=3.2 Hz), 4.62 (1H, d, J=12 Hz), 4.04 (1H, dd, J=9.6, 3.2 Hz), 3.94 (1H, dd, J=10, 3.2 Hz), 3.91-3.89 (1H, m), 3.84 (1H, br.t, J=6.4 Hz), 3.44 (1H, dd, J=10, 6.4 Hz), 3.37 (3H, s), 3.34 (1H, dd, J=10, 6.4 Hz), 3.27 (3H, s) ppm.

(Step b) Synthesis of Compound 2-4

To a solution of compound 2-3 (733 mg, 1.53 mmol) in acetic anhydride (20 mL) was added a solution of concentrated sulfuric acid (0.03 mL) in acetic anhydride (10 mL) under ice-cooling, and the mixture was stirred for 20 min. Saturated aqueous sodium hydrogen carbonate solution was added, and the mixture was neutralized and diluted with ethyl acetate. The organic layer was washed successively with saturated aqueous sodium hydrogen carbonate solution, water and saturated brine, and dried over anhydrous magnesium sulfate. After filtration, the solvent was evaporated by concentration under reduced pressure.

To a solution of the residue in methanol (10 mL) was added sodium methoxide (90 mg, 1.7 mmol) at room temperature, and the mixture was stirred for 30 min. The mixture was acidified with cation exchange resin (Dowex 50W-X8) and filtered, and the solvent was evaporated by concentration under reduced pressure. The residue was purified by silica gel column chromatography (20 g, hexane-ethyl acetate=3:1) to give compound 2-4 (652 mg, 92%) as a white powder.

IR (KBr): $v_{max}$=3420 (br.s, OH), 1605 (w, arom.), 1495 (m, arom.), 1100 (br.s, C—O), 735 (s), 695 (s) cm$^{-1}$.

(Step c) Synthesis of Compound 2-5

To a solution of compound 2-4 (602 mg, 1.30 mmol) in dichloromethane (20 mL) was added diethylaminosulfurtrifluoride (0.35 mL, 2.65 mmol) at −40° C. After stirring at room temperature for 1 hr, the mixture was cooled to −40° C. again, and methanol (1 mL) was added. The solvent was evaporated by concentration under reduced pressure, and the residue was diluted with ethyl acetate. The organic layer was washed successively with saturated aqueous sodium hydrogen carbonate solution, water and saturated brine, and dried over anhydrous magnesium sulfate. After filtration, the solvent was evaporated by concentration under reduced pressure, and the residue was purified by silica gel column chromatography (15 g, hexane-ethyl acetate=40:3) to give compound 2-5 (554 mg, α:β=ca. 1:1, 91%) as a colorless oil.

$^1$H NMR (400 MHz, CDCl$_3$): δ=5.59 (1H, dd, J=54, 3.2 Hz, α-isomer), 5.18 (1H, dd, J=53, 6.8 Hz, β-isomer) ppm (Step d) Synthesis of Compound 2-7

To a solution of compound 2-6 (438 mg, 0.474 mmol) known in the reference (H. Takikawa et al. Tetrahedron, 1998, 54, 3141-3150) in dry tetrahydrofuran (15 ml) were added dried molecular sieves (4.03 g), tin chloride (II) (270 mg, 1.42 mmol) and silver perchlorate (300 mg, 1.45 mmol), and the mixture was stirred for 2 hr in a flask in shading. The reaction mixture was cooled to −18° C., and a solution of compound 2-5 (252 mg, 0.540 mmol) in dry tetrahydrofuran (10 mL) was added. The temperature was allowed to rise to 10° C. over 2 hr with stirring, diethyl ether (25 mL) was added, and the mixture was filtered. The filtrate was washed with water and saturated brine, and dried over anhydrous magnesium sulfate. After filtration, the solvent was evaporated by concentration under reduced pressure, and the residue was purified by silica gel column chromatography (20 g, hexane-ethyl acetate=10:1) to give compound 2-7 (172 mg, 26%) as a colorless oil.

$n_D^{24}$=1.4952.

IR (film): $v_{max}$=3360 (m, NH), 1680 (br.s, C=O), 1610 (w, arom.), 1520 (m), 1500 (m, arom.), 1250 (s, t-Bu, Si-Me), 1105 (br.s, C—O), 1060 (br.s, C—O), 835 (s), 780 (s), 735 (br.m), 695 (s) cm$^{-1}$.

$^1$H NMR (400 MHz, CDCl$_3$): δ=7.38-7.26 (15H, m), 6.26 (1H, d, J=8.0 Hz), 4.96 (1H, d, J=12 Hz), 4.800 (1H, d, J=4.0 Hz), 4.798 (2H, d, J=12 Hz), 4.72 (1H, d, J=12 Hz), 4.64 (1H, d, J=12 Hz), 4.62 (1H, d, J=12 Hz), 4.10-3.98 (3H, m), 3.93-3.85 (3H, m), 3.79 (1H, br.d, J=7.6 Hz), 3.69 (1H, dd, J=11, 2.8 Hz), 3.64-3.60 (1H, m), 3.44 (1H, dd, J=9.2, 6.0 Hz), 3.29 (1H, dd, J=9.2, 5.2 Hz), 3.26 (3H, s), 2.05-2.00 (2H, m), 1.59-1.18 (72H, m), 0.90 (9H, s), 0.884 (9H, s), 0.879 (3H, t, J=6.8 Hz), 0.07 (3H, s), 0.03 (3H, s), 0.024 (3H, s), 0.016 (3H, s) ppm.

(Step e) Synthesis of Compound 2-8

To a solution of compound 2-7 (126 mg, 0.0919 mmol) in tetrahydrofuran (5 mL) was added a solution (1.0 M, 370 μL, 0.37 mmol) of tetra-n-butylammonium fluoride in tetrahydrofuran at room temperature, and the mixture was stirred for 18 hr. Water was added, and the mixture was extracted with ethyl acetate. The organic layer was washed with water and saturated brine, and dried over anhydrous magnesium sulfate. After filtration, the solvent was evaporated by concentration under reduced pressure, and the residue was purified by silica gel column chromatography (15 g, hexane-ethyl acetate=7:3) to give compound 2-8 (98 mg, 93%) as a white solid.

IR (KBr): $v_{max}$=3420 (br.s, OH), 3320 (br.m, NH), 1645 (s, C=O), 1620 (s), 1540 (br.s), 1500 (w, arom.), 1100 (br.s, C—O), 1060 (br.s, C—O), 735 (br.s), 695 (s) cm$^{-1}$.

$^1$H NMR (400 MHz, CDCl$_3$): δ=7.40-7.28 (15H, m), 6.40 (1H, d, J=8.8 Hz), 4.94 (1H, d, J=12 Hz), 4.90 (1H, d, J=12 Hz), 4.84 (1H, d, J=4.0 Hz), 4.77 (2H, s), 4.68 (1H, d, J=12 Hz), 4.61 (1H, d, J=12 Hz), 4.23-4.17 (1H, m), 4.05 (1H, dd, J=10, 3.6 Hz), 3.94 (1H, br.s), 3.90-3.84 (2H, m), 3.82 (1H, br.t, J=6.8 Hz), 3.79-3.77 (1H, m), 3.52-3.44 (2H, m), 3.41 (1H, dd, J=10, 6.4 Hz), 3.34 (1H, dd, J=8.4, 6.4 Hz), 3.26 (3H, s), 2.18-2.12 (3H, m), 1.64-1.15 (73H, m), 0.88 (6H, t, J=6.8 Hz) ppm.

(Step f) Synthesis of Compound 2-9

To a solution of compound 2-8 (73 mg, 0.064 mmol) in tetrahydrofuran-ethanol-chloroform (5:8:2, 15 mL) was added palladium hydroxide-activated carbon (20%, wet, 33 mg) at room temperature. After stirring for 17 hr under a hydrogen atmosphere, the mixture was diluted with chloroform-methanol (5:1). After filtration, the solvent was evaporated by concentration under reduced pressure, and the residue was purified by silica gel column chromatography (6 g, hexane-ethyl acetate=25:2) to give compound 2-9 (43 mg, 77%) as a white powder.

IR (KBr): $v_{max}$=3440 (br.s, OH), 3280 (w, NH), 1640 (br.s, C=O), 1540 (br.m), 1080 (br.s, C—O), 720 (w) cm$^{-1}$.

$^1$H NMR (400 MHz, C$_5$D$_5$N): δ=8.44 (1H, d, J=8.8 Hz), 7.05 (1H, br.s), 6.74 (1H, br.s), 6.45 (1H, d, J=6.4 Hz), 6.39 (1H, br.s), 6.08 (1H, br.s), 5.52 (1H, d, J=4.0 Hz), 5.28-5.22 (1H, m), 4.64 (1H, dd, J=10, 5.6 Hz), 4.65-4.58 (1H, m), 4.46 (1H, t, J=6.4 Hz), 4.40-4.28 (4H, m), 4.14-4.08 (1H, m), 3.97 (1H, dd, J=9.6, 5.6 Hz), 3.94 (1H, dd, J=9.6, 6.4 Hz), 3.33 (3H, s), 2.42 (2H, t, J=7.2 Hz), 2.33-2.20 (1H, m), 1.95-1.60 (5H, m), 1.48-1.16 (68H, m), 0.84 (3H, t, J=6.8 Hz) ppm.

HRFABMS: calcd for C$_{51}$H$_{102}$O$_9$N ([M+H]$^+$) 872.7555. found 872.7553.

Example 2

Synthesis of Compound 3-4

Compound 3-4 was synthesized according to the following scheme.

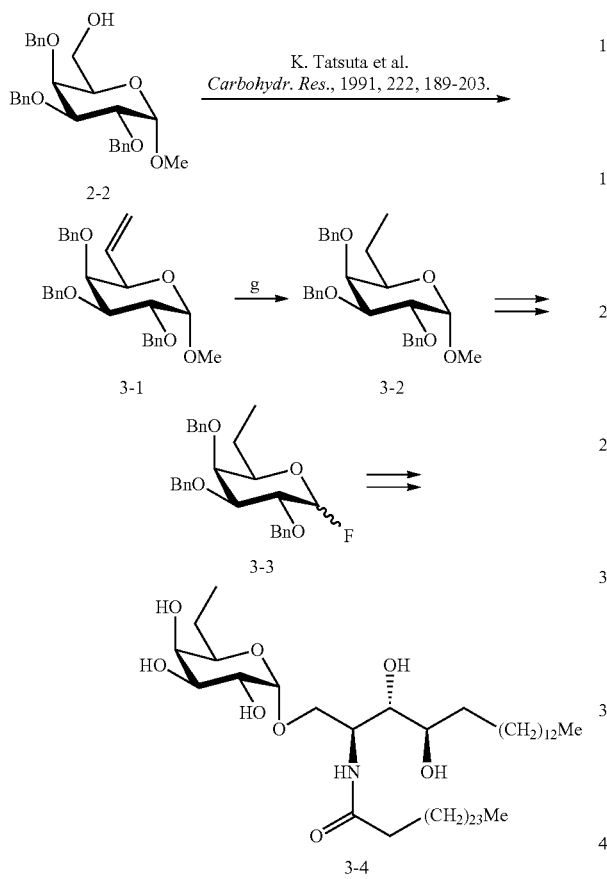

(Step g) Synthesis of Compound 3-2

To a solution of compound 3-1 (1.12 g, 2.43 mmol) known in the reference (K. Tatsuta et al. Carbohydr. Res., 1991, 222, 189-203) and hydrazine monohydrate (10 ml, 20.6 mmol) in ethanol (50 mL) was slowly added aqueous hydrogen peroxide (30%, 4 ml) at room temperature over 3 hr, and the reaction mixture was stirred at room temperature for 18 hr. Saturated aqueous sodium thiosulfate solution (20 mL) was added under ice-cooling, and the mixture was stirred for 30 min. The mixture was diluted with ethyl acetate, the organic layer was washed successively with water, saturated aqueous sodium thiosulfate solution and saturated brine, and dried over anhydrous magnesium sulfate. After filtration, the solvent was evaporated by concentration under reduced pressure, and the residue was purified by silica gel column chromatography (20 g, hexane-ethyl acetate=20:1) to give compound 3-2 (981 mg, 87%) as a colorless oil.

$n_D^{22}$=1.5163.

IR (film): $v_{max}$=1605 (w, arom.), 1500 (s, arom.), 1100 (br.s, C—O), 1050 (br.s, C—O), 740 (s), 700 (s) cm$^{-1}$.

$^1$H NMR (400 MHz, CDCl$_3$): δ=7.42-7.25 (15H, m), 4.99 (1H, d, J=11 Hz), 4.89 (1H, d, J=12 Hz), 4.84 (1H, d, J=12 Hz), 4.75 (1H, d, J=12 Hz), 4.70 (1H, d, J=12 Hz), 4.66 (1H, d, J=4.0 Hz), 4.65 (1H, d, J=11 Hz), 4.05 (1H, dd, J=10, 4.0 Hz), 3.92 (1H, dd, J=10, 2.8 Hz), 3.72 (1H, d, J=2.8 Hz), 3.50 (1H, dd, J=8.4, 6.0 Hz), 3.35 (3H, s), 1.66 (1H, ddq, J=14, 7.2, 6.0 Hz), 1.37 (1H, m), 0.81 (3H, t, J=7.2 Hz) ppm.

Synthesis of Compound 3-4

By a method similar to conversion of compound 2-3 to compound 2-9, compound 3-4 was obtained as a white powder in 5 steps via compound 3-2 to compound 3-3.

$^1$H NMR (400 MHz, C$_5$D$_5$N): δ=8.49 (1H, d, J=8.8 Hz), 6.98 (1H, br.s), 6.59 (1H, br.s), 6.44 (1H, br.d, J=7.2 Hz), 6.13 (2H, br.s), 5.48 (1H, d, J=3.6 Hz), 5.33-5.26 (1H, m), 4.64 (1H, dd, J=10, 5.6 Hz), 4.60-4.54 (1H, m), 4.38-4.27 (3H, m), 4.27 (1H, dd, J=10, 4.8 Hz), 4.17 (1H, br.s), 3.99 (1H, t, J=6.8 Hz), 2.44 (2H, t, J=6.8 Hz), 2.35-2.25 (1H, m), 2.15-2.03 (1H, m), 1.98-1.77 (5H, m), 1.74-1.61 (1H, m), 1.47-1.16 (66H, m), 1.05 (3H, t, J=7.2 Hz), 0.84 (6H, t, J=7.2 Hz) ppm.

Example 3

Synthesis of Compound 3-7

Compound 3-7 was synthesized according to the following scheme.

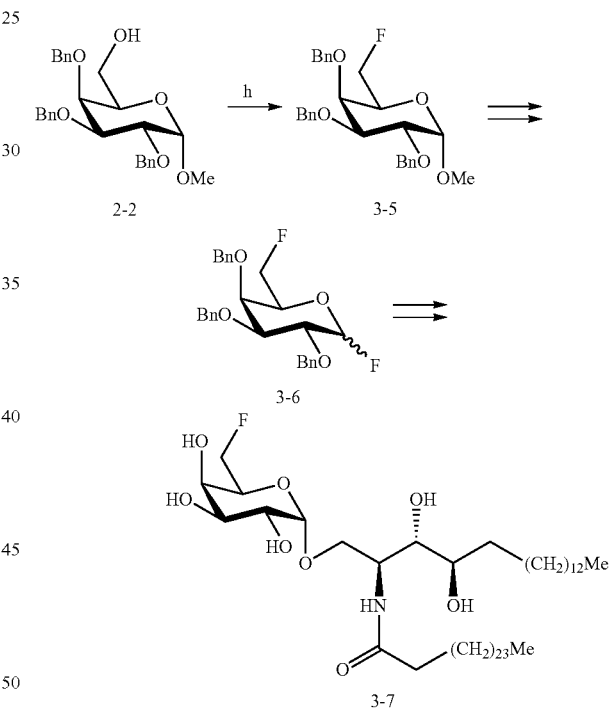

(Step h) Synthesis of Compound 3-5

To a solution of compound 2-2 (2.03 g, 4.37 mmol) known in the reference (T. J. Lucas et al., Carbohydr. Res., 1975, 39, 39-45) and triethylamine (1.85 mL, 13.3 mmol) in dichloromethane (30 mL) was slowly added diethylamino sulfur trifluoride (1.20 mL, 9.08 mmol) at −40° C. The reaction mixture was stirred for 5 hr with heating under reflux, methanol (2 mL) was added under ice-cooling, and the mixture was stirred for 30 min. The mixture was diluted with ethyl acetate, and the organic layer was washed successively with water, saturated aqueous sodium hydrogen carbonate solution and saturated brine, and dried over anhydrous magnesium sulfate. After filtration, the solvent was evaporated by concentration under reduced pressure, and the residue was purified by silica gel column chromatography (30 g, hexane-ethyl acetate=8:1) to give compound 3-5 (688 mg, 34%) as a colorless oil. $n_D^{22}$=1.5169.

IR (film): $v_{max}$=1600 (w, arom.), 1500 (s, arom.), 1100 (br.s, C—O), 1040 (br.s, C—O), 740 (s), 700 (s) cm$^{-1}$.

$^1$H NMR (400 MHz, CDCl$_3$): δ=7.42-7.24 (15H, m), 4.97 (1H, d, J=12 Hz), 4.89 (1H, d, J=12 Hz), 4.85 (1H, d, J=12 Hz), 4.75 (1H, d, J=12 Hz), 4.70 (1H, d, J=12 Hz), 4.69 (1H, d, J=4.0 Hz), 4.60 (1H, d, J=12 Hz), 4.44 (1H, ddd, J=48, 9.2, 6.0 Hz), 4.27 (1H, ddd, J=46, 9.2, 5.2 Hz), 4.04 (1H, dd, J=10, 4.0 Hz), 4.00-3.91 (2H, m), 3.89 (1H, br.s), 3.37 (3H, s) ppm.

Synthesis of Compound 3-7

By a method similar to conversion of compound 2-3 to compound 2-9, compound 3-7 was obtained as a white powder in 5 steps via compound 3-5 to compound 3-6.

$^1$H NMR (400 MHz, C$_5$D$_5$N): δ=8.47 (1H, d, J=8.8 Hz), 7.15 (1H, br.s), 6.95 (1H, br.s), 6.67 (1H, br.s), 6.48 (1H, br.s), 6.13 (1H, br.s), 5.56 (1H, d, J=4.0 Hz), 5.32-5.26 (1H, m), 5.02 (1H, ddd, J=49, 10, 6.8 Hz), 4.95 (1H, ddd, J=46, 10, 4.4 Hz), 4.68 (1H, dd, J=10, 5.6 Hz), 4.61 (1H, dd, J=10, 4.4 Hz), 4.54-4.47 (1H, m), 4.39 (1H, dd, J=9.6, 3.2 Hz), 4.31-4.27 (3H, m), 4.12 (1H, t, J=6.8 Hz), 2.42 (2H, br.t, J=7.2 Hz), 2.34-2.25 (1H, m), 1.97-1.84 (2H, m), 1.80 (2H, quint., J=7.2 Hz), 1.73-1.60 (1H, m), 1.48-1.15 (68H, m), 0.84 (6H, t, J=6.8 Hz) ppm.

Example 4

Synthesis of Compound 3-10

Compound 3-10 was synthesized according to the following scheme.

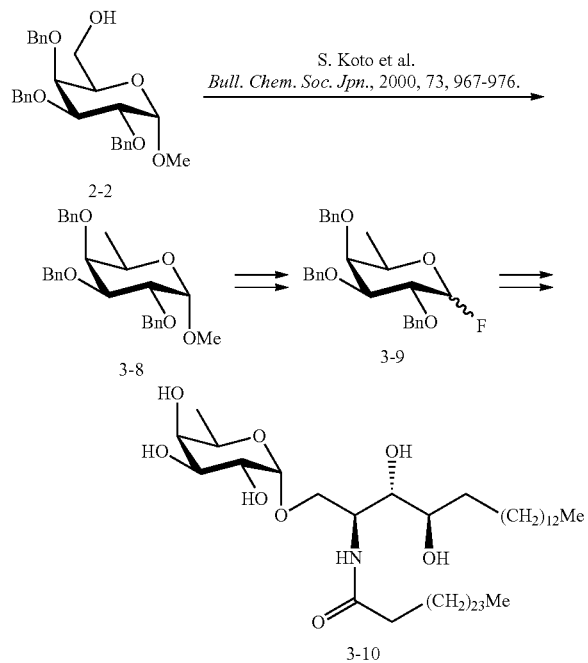

Synthesis of Compound 3-10

By a method similar to conversion of compound 2-3 to compound 2-9, compound 3-10 was obtained as a white powder in 5 steps from compound 3-8 known in the reference (S. Koto et al. Bull. Chem. Soc. Jpn., 2000, 73, 967-976) via compound 3-9.

$^1$H NMR (400 MHz, C$_5$D$_5$N): δ=8.46 (1H, d, J=8.8 Hz), 6.99 (1H, br.s), 6.44 (1H, br.s), 6.23 (1H, br.s), 6.14 (2H, br.s), 5.48 (1H, d, J=4.0 Hz), 5.32-5.27 (1H, m), 4.65 (1H, dd, J=10, 5.6 Hz), 4.57 (1H, dd, J=10, 4.4 Hz), 4.38 (1H, dd, J=10, 4.4 Hz), 4.34-4.27 (4H, m), 4.08 (1H, br.d, J=2.4 Hz), 2.44 (2H, br.t, J=6.8 Hz), 2.35-2.26 (1H, m), 1.97-1.83 (2H, m), 1.82 (2H, quint., J=6.8 Hz), 1.74-1.63 (1H, m), 1.50 (3H, d, J=6.4 Hz), 1.47-1.17 (66H, m), 0.85 (6H, t, J=6.8 Hz) ppm.

Example 5

Synthesis of Compound 3-13

Compound 3-13 was synthesized according to the following scheme.

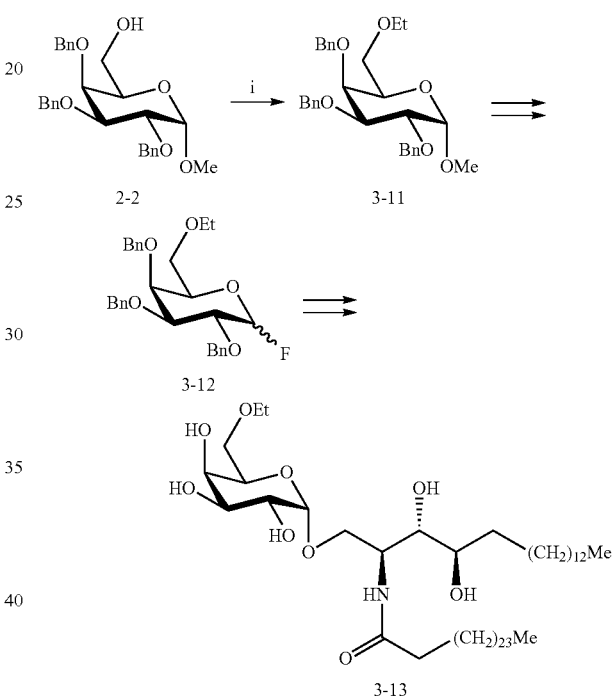

(Step i) Synthesis of Compound 3-11

To a solution of compound 2-2 (587 mg, 1.26 mmol) known in the reference (T. J. Lucas et al., Carbohydr. Res., 1975, 39, 39-45) in N,N-dimethylformamide-tetrahydrofuran (1:1, 20 mL) was added sodium hydride (60% mineral oil suspension, 158 mg, 3.95 mmol) under ice-cooling. After stirring for 10 min under ice-cooling, ethyl bromide (295 μL, 3.95 mmol) and a catalytic amount of tetra-n-butylammonium iodide were added, and the mixture was stirred at room temperature for 12 hr. Water was added, and the mixture was extracted with ethyl acetate. The organic layer was washed successively with water and saturated brine, and dried over anhydrous magnesium sulfate. After filtration, the solvent was evaporated by concentration under reduced pressure, and the residue was purified by silica gel column chromatography (20 g, hexane-ethyl acetate=8:1) to give compound 3-11 (606 mg, 98%) as a colorless oil.

$n_D^{23}$=1.5170.

IR (film): $v_{max}$=1605 (w, arom.), 1495 (m, arom.), 1115 (br.s, C—O), 1050 (br.s, C—O), 735 (br.s), 700 (s) cm$^{-1}$.

$^1$H NMR (400 MHz, CDCl$_3$): δ=7.40-7.24 (15H, m), 4.95 (1H, d, J=12 Hz), 4.85 (1H, d, J=12 Hz), 4.83 (1H, d, J=12

Hz), 4.74 (1H, d, J=12 Hz), 4.685 (1H, d, J=12 Hz), 4.682 (1H, d, J=3.2 Hz), 4.62 (1H, d, J=12 Hz), 4.06-4.02 (1H, m), 3.96-3.92 (2H, m), 3.85 (1H, br t, J=6.6 Hz), 3.49-3.42 (3H, m), 3.38-3.34 (1H, m), 3.37 (3H, s), 1.14 (3H, t, J=7.2 Hz) ppm Synthesis of Compound 3-13

By a method similar to conversion of compound 2-3 to compound 2-9, compound 3-13 was obtained as a white powder in 5 steps via compound 3-11 to compound 3-12.

$^1$H NMR (500 MHz, CDCl$_3$): δ=8.43 (1H, d, J=9.0 Hz), 7.02 (1H, br s), 6.69 (1H, br s), 6.43 (1H, d, J=6.5 Hz), 6.36 (1H, br s), 6.07 (1H, d, J=5.5 Hz), 5.51 (1H, d, J=3.5 Hz), 5.23 (1H, dq, J=8.0, 4.0 Hz), 4.63 (1H, dd, J=10, 5.0 Hz), 4.63-4.58 (1H, m), 4.45 (1H, t, J=6.5 Hz), 4.40-4.28 (4H, m), 4.36 (1H, dd, J=10, 5.0 Hz), 4.04 (1H, dd, J=10, 6.5 Hz), 3.96 (1H, dd, J=10, 6.5 Hz), 3.55-3.45 (2H, m), 2.42 (2H, dt, J=7.0, 2.0 Hz), 2.30-2.23 (1H, m), 1.96-1.84 (2H, m), 1.80 (2H, quint., J=7.0 Hz), 1.72-1.61 (1H, m), 1.48-1.17 (66H, m), 1.14 (3H, t, J=7.0 Hz), 0.84 (6H, t, J=7.0 Hz) ppm.

Example 6

Synthesis of Compound 3-16

Compound 3-16 was synthesized according to the following scheme.

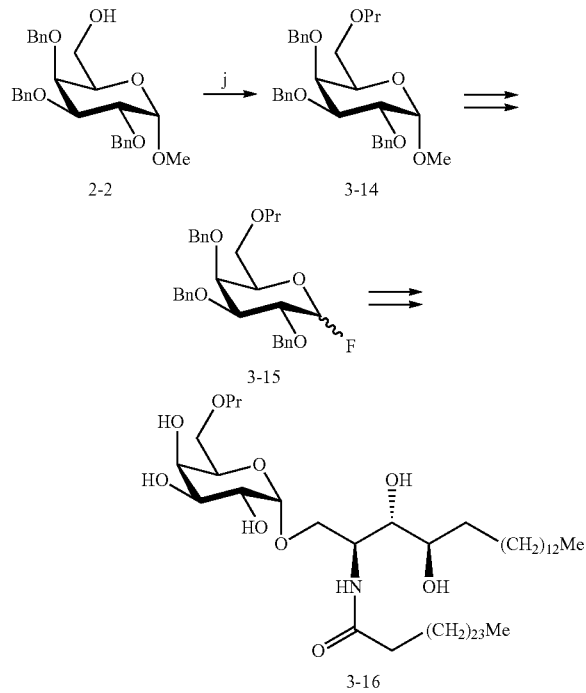

(Step j) Synthesis of Compound 3-14

To a solution of compound 2-2 (630 mg, 1.36 mmol) known in the reference (T. J. Lucas et al., Carbohydr. Res., 1975, 39, 39-45) in N,N-dimethylformamide-tetrahydrofuran (1:1, 20 mL) was added sodium hydride (60% mineral oil suspension, 170 mg, 4.25 mmol) under ice-cooling. After stirring for 10 min under ice-cooling, 1-propyl bromide (390 μL, 4.28 mmol) and a catalytic amount of tetra-n-butylammonium iodide were added, and the mixture was stirred at room temperature for 12 hr. Water was added, and the mixture was extracted with ethyl acetate. The organic layer was washed successively with water and saturated brine, and dried over anhydrous magnesium sulfate. After filtration, the solvent was evaporated by concentration under reduced pressure, and the residue was purified by silica gel column chromatography (20 g, hexane-ethyl acetate=40:3) to give compound 3-14 (647 mg, 94%) as a colorless oil.

$n_D^{23}$=1.5177.

IR (film): $v_{max}$=1605 (w, arom.), 1495 (m, arom.), 1110 (br.s, C—O), 1050 (br.s, C—O), 740 (br.s), 700 (s) cm$^{-1}$.

$^1$H NMR (400 MHz, CDCl$_3$): δ=7.40-7.24 (15H, m), 4.96 (1H, d, J=12 Hz), 4.85 (1H, d, J=12 Hz), 4.83 (1H, d, J=12 Hz), 4.74 (1H, d, J=12 Hz), 4.685 (1H, d, J=12 Hz), 4.680 (1H, d, J=4.0 Hz), 4.61 (1H, d, J=12 Hz), 4.06-4.01 (1H, m), 3.96-3.92 (2H, m), 3.86 (1H, t, J=6.4 Hz), 3.45 (2H, d, J=6.4 Hz), 3.40-3.34 (1H, m), 3.37 (3H, s), 3.26 (1H, dt, J=9.6, 7.2 Hz), 1.53 (1H, sext., J=7.2 Hz), 0.89 (3H, t, J=7.2 Hz) ppm.

Synthesis of Compound 3-16

By a method similar to conversion of compound 2-3 to compound 2-9, compound 3-16 was obtained as a white powder in 5 steps via compound 3-14 to compound 3-15.

$^1$H NMR (500 MHz, CDCl$_3$): δ=8.43 (1H, d, J=8.5 Hz), 7.02 (1H, br s), 6.69 (1H, br s), 6.42 (1H, d, J=6.5 Hz), 6.35 (1H, br s), 6.08 (1H, d, J=5.5 Hz), 5.52 (1H, d, J=4.0 Hz), 5.25 (1H, dq, J=8.0, 4.0 Hz), 4.65 (1H, dd, J=11, 5.5 Hz), 4.66-4.58 (1H, m), 4.46 (1H, t, J=5.5 Hz), 4.42-4.28 (4H, m), 4.36 (1H, dd, J=11, 5.5 Hz), 4.07 (1H, dd, J=10, 6.0 Hz), 3.97 (1H, dd, J=10, 6.0 Hz), 3.58-3.48 (2H, m), 2.43 (2H, dt, J=7.0, 2.0 Hz), 2.31-2.24 (1H, m), 1.96-1.84 (2H, m), 1.81 (2H, quint., J=7.0 Hz), 1.73-1.64 (1H, m), 1.56 (2H, sext., J=7.0 Hz), 1.46-1.16 (66H, m), 0.87 (3H, t, J=7.0 Hz), 0.847 (3H, t, J=7.0 Hz), 0.845 (3H, t, J=7.0 Hz) ppm.

Experimental Example 1

Biological Activity Test of Compound 2-9, Compound 3-4, Compound 3-7 and Compound 3-10

DMSO solutions (1 mg/mL concentration) of α-GalCer, carba-glycolipid A, compound 2-9, compound 3-4, compound 3-7 and compound 3-10 were prepared. The above-mentioned DMSO solutions were diluted with saline (manufactured by Otsuka Pharmaceutical Co., Ltd.) containing 0.5% Tween 20 (Bio-Rad) such that the dose would be 100 μg/kg body weight when 200 μL is administered to one mouse from the tail vein.

Each of the prepared solutions (200 μL) of carba-glycolipid A, compound 2-9, compound 3-4, compound 3-7 and compound 3-10 was injected to C57BL/6 mice (5 per group) from the tail vein. α-GalCer was used as a control substance, and 200 μL of α-GalCer solution prepared to a dose of 100 μg/kg body weight according to a similar method was injected from the tail vein. A group administered with a medium (200 μL of saline containing 0.5% Tween 20) was taken as a negative control. The blood (80 μL) was taken from the orbital plexus venosus 6, 12, 24, 36, 48 and 60 hr after administration, and the serum was prepared.

The content of IFN-γ in the serum after lapse of 6, 12, 24, 36, 48 and 60 hr from the administration was measured by sandwich ELISA (ENDOGEN). The measurement results (average value) of the IFN-γ production level and the standard deviation (STDEV) thereof are shown in FIG. 1.

Figure 2:
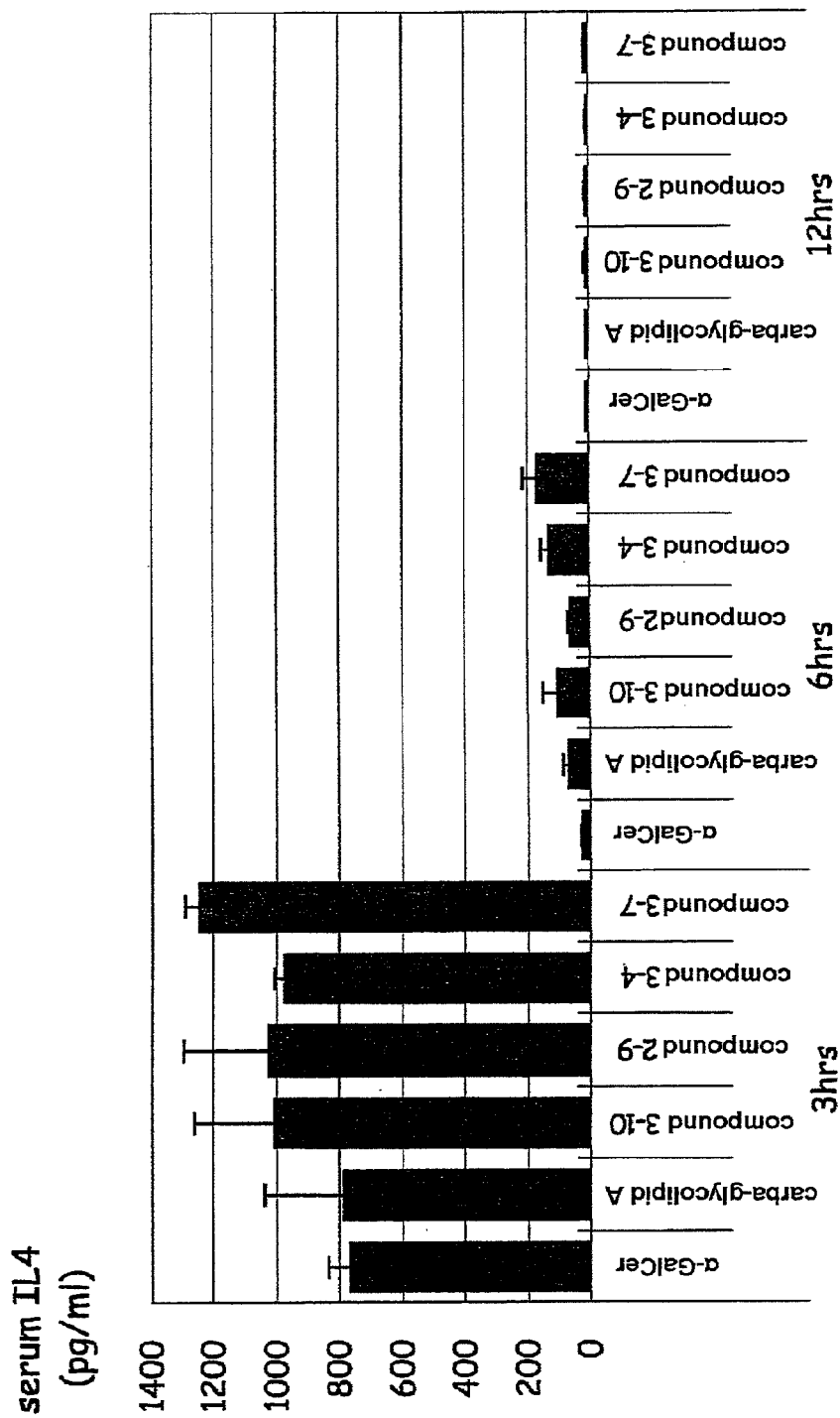
FIG. 2 shows the concentration of IL-4 in the serum after lapse of indicated time from the administration of synthetic glycolipid to mouse in vivo.

The content of IL-4 in the serum after lapse of 3, 6 and 12 hr from the administration was measured by Cytometric bead array system (BD Biosciences), which is one kind of the ELISA method. The measurement results (average value) of the IL-4 production level and the standard deviation (STDEV) thereof are shown in FIG. 2.

Figure 3:
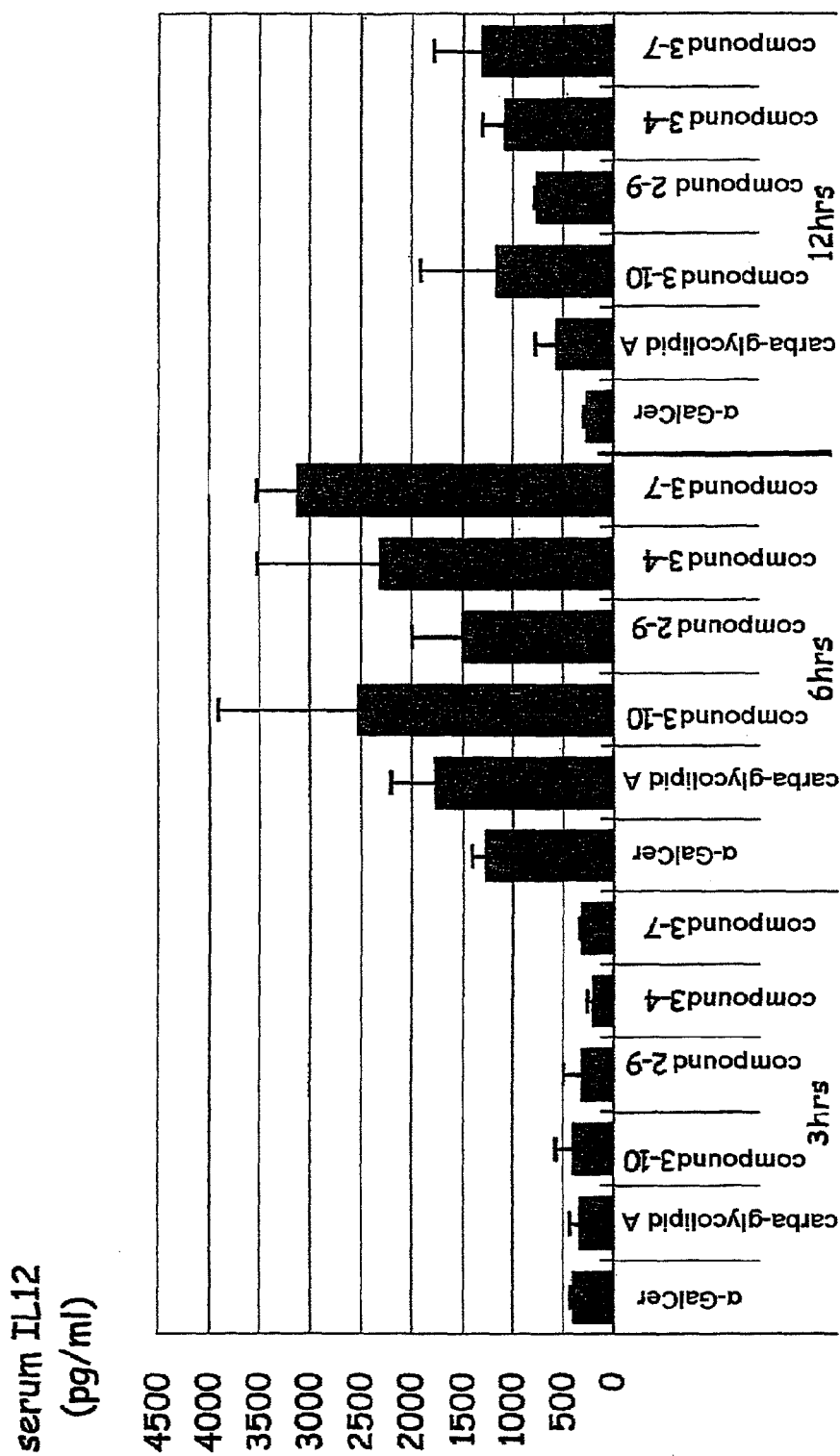
FIG. 3 shows the concentration of IL-12 in the serum after lapse of indicated time from the administration of synthetic glycolipid to mouse in vivo.

The content of IL-12 in the serum after lapse of 3, 6 and 12 hr from the administration was measured by Cytometric bead array system (BD Biosciences), which is one kind of the ELISA method. The measurement results (average value) of the IL-12 production level (average value) and the standard deviation (STDEV) thereof are shown in FIG. 3.

From the above-mentioned results, all of compound 2-9, compound 3-4, compound 3-7 and compound 3-10 induced production of a larger amount of IFN-γ than α-GalCer and carba-glycolipid A. Particularly, compound 2-9 induced the production most strongly. In addition, all of these compounds also induced production of IL-12 in the same level as or up to 3-fold level as compared with α-GalCer. On the other hand, the production level of IL-4 did not show much difference. Therefrom it was shown that compound 2-9, compound 3-4, compound 3-7 and compound 3-10 selectively induced production of IFN-γ in larger amounts as compared to α-GalCer and carba-glycolipid A.

Experimental Example 2

Biological Activity Test of Compound 2-9, Compound 3-4, Compound 3-7, Compound 3-10, Compound 3-13 and Compound 3-16

Figure 4:
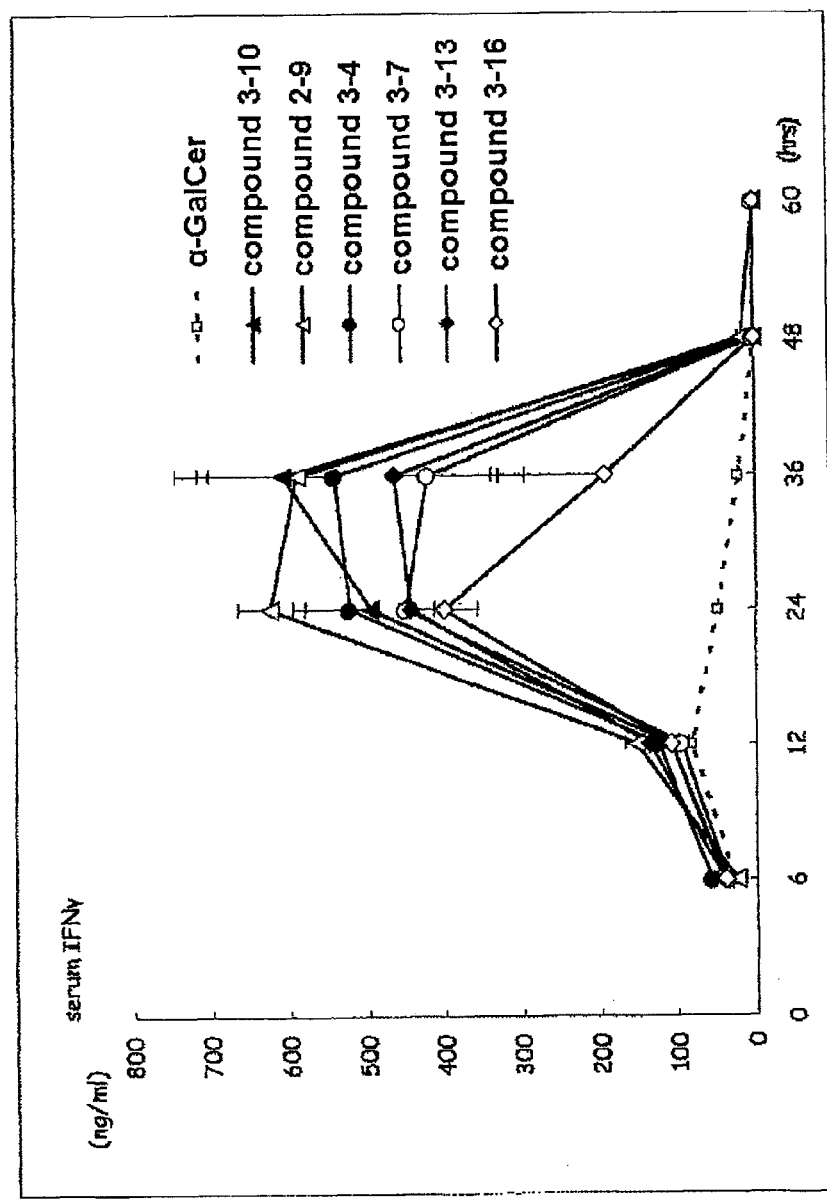
FIG. 4 shows the concentration of IFN-γ in the serum after lapse of indicated time from the administration of synthetic glycolipid to the tail of mouse by intravenous injection.

By a method similar to Experimental Example 1, the content of IFN-γ in the serum after lapse of 6, 12, 24, 36, 48 and 60 hr from the administration of α-GalCer, compound 2-9, compound 3-4, compound 3-7, compound 3-10, compound 3-13 and compound 3-16 was measured. The measurement results (average value) of the IFN-γ production level and the standard deviation (STDEV) thereof are shown in FIG. 4.

Figure 6:
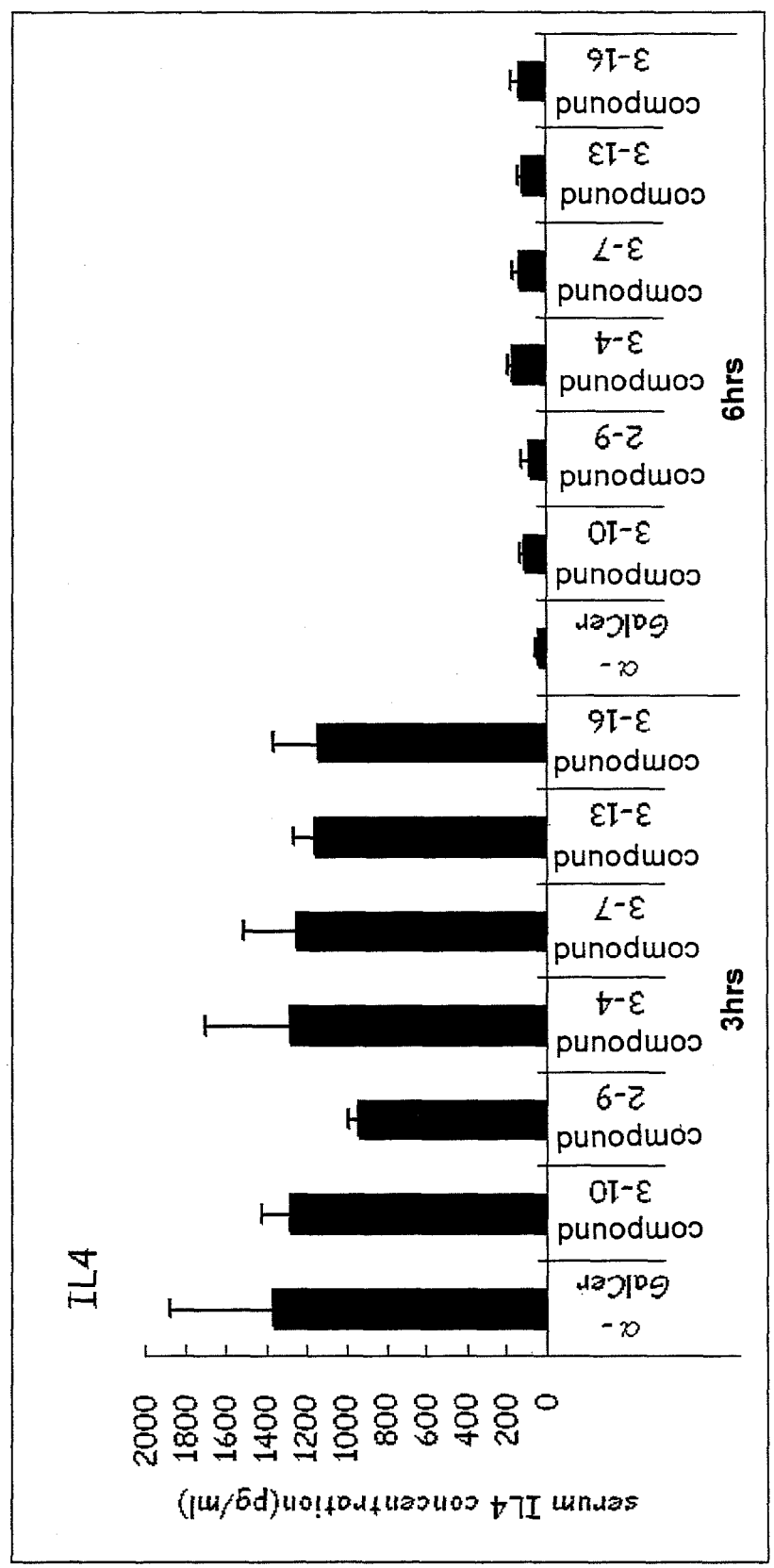
FIG. 6 shows the concentration of IL-4 in the serum after lapse of indicated time from the administration of synthetic glycolipid to the tail of mouse by intravenous injection.

By a method similar to Experimental Example 1, the content of IL-4 in the serum after lapse of 3 and 6 hr from the administration of α-GalCer, compound 2-9, compound 3-4, compound 3-7, compound 3-10, compound 3-13 and compound 3-16 was measured. The measurement results (average value) of the IL-4 production level and the standard deviation (STDEV) thereof are shown in FIG. 6.

Figure 8:
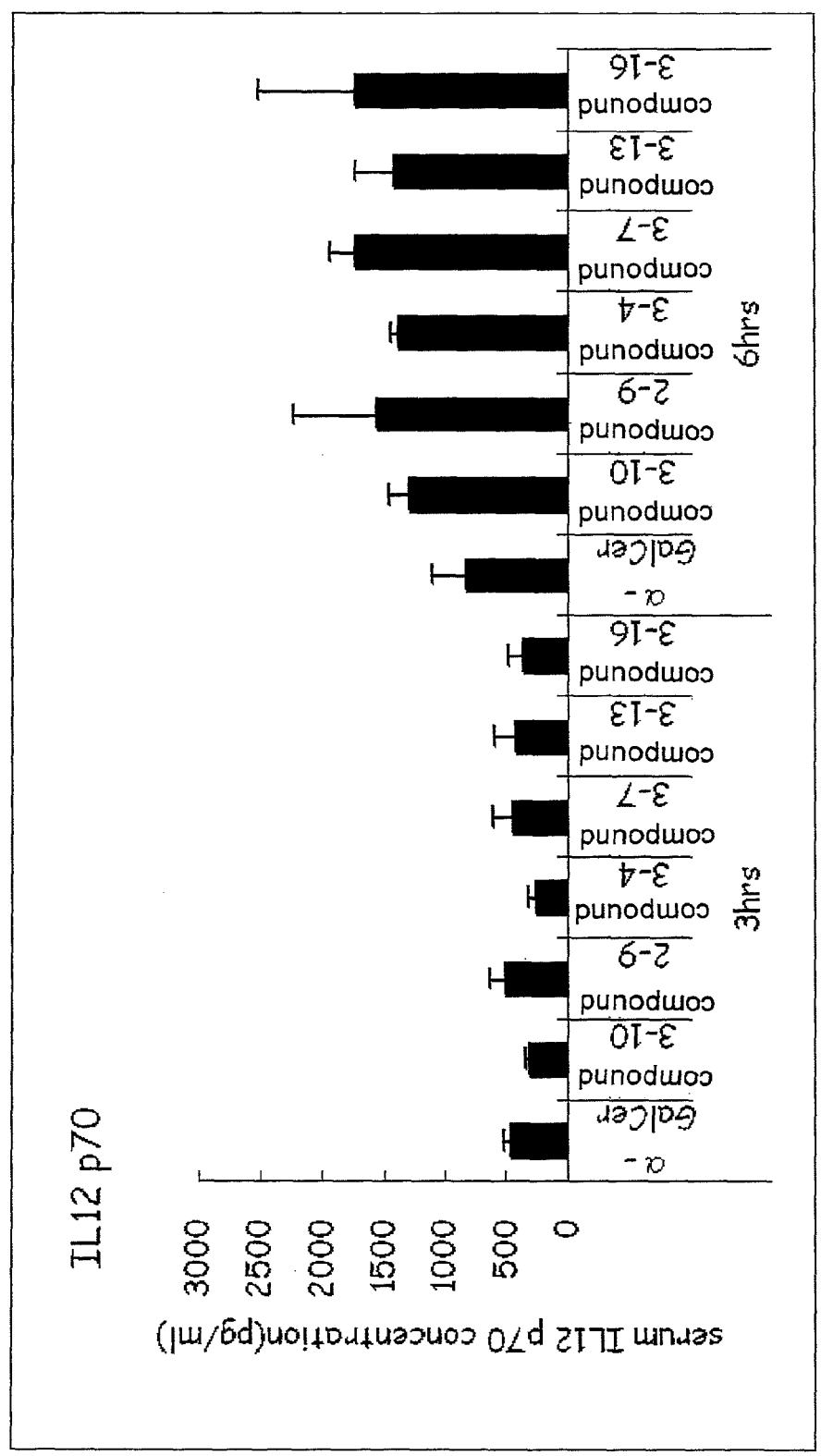
FIG. 8 shows the concentration of IL-12 in the serum after lapse of indicated time from the administration of synthetic glycolipid to the tail of mouse by intravenous injection.

By a method similar to Experimental Example 1, the content of IL-12(p70) in the serum after lapse of 3 and 6 hr from the administration of α-GalCer, compound 2-9, compound 3-4, compound 3-7, compound 3-10, compound 3-13 and compound 3-16 was measured. The measurement results (average value) of the IL-12 production level and the standard deviation (STDEV) thereof are shown in FIG. 8.

From the above-mentioned results, all of compound 2-9, compound 3-4, compound 3-7, compound 3-10, compound 3-13 and compound 3-16 induced production of a larger amount of IFN-γ than α-GalCer. Particularly, compound 2-9 induced the production most strongly. In addition, all of these compounds also induced production of IL-12 in the same level as or up to 2-fold level as compared with α-GalCer. On the other hand, the production level of IL-4 did not show much difference. Therefrom it was shown that compound 2-9, compound 3-4, compound 3-7, compound 3-10, compound 3-13 and compound 3-16 selectively induced production of IFN-γ in larger amounts as compared to α-GalCer.

Experimental Example 3

Biological Activity Test of Compound 2-9

Figure 5:
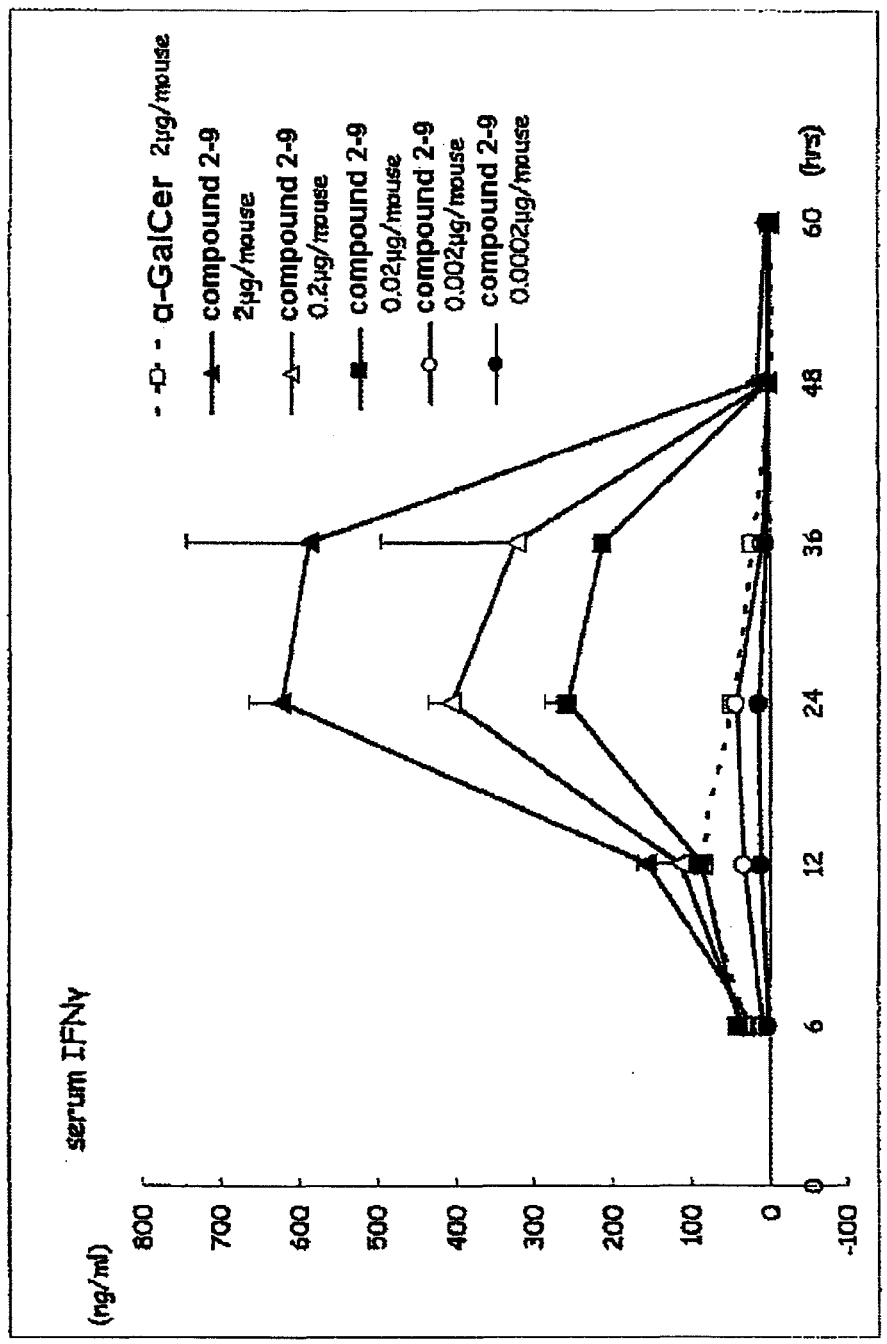
FIG. 5 shows the concentration of IFN-γ in the serum after lapse of indicated time from the administration of synthetic glycolipid to the tail of mouse by intravenous injection.

By a method similar to Experimental Example 1 except that the dose of α-GalCer was 2 μg/mouse and the dose of compound 2-9 was 2 μg/mouse, 0.2 μg/mouse, 0.02 μg/mouse, 0.002 μg/mouse or 0.0002 μg/mouse, the content of IFN-γ in the serum after lapse of 6, 12, 24, 36, 48 and 60 hr from the administration of α-GalCer and compound 2-9 was measured. The measurement results (average value) of the IFN-γ production level and the standard deviation (STDEV) thereof are shown in FIG. 5.

Figure 7:
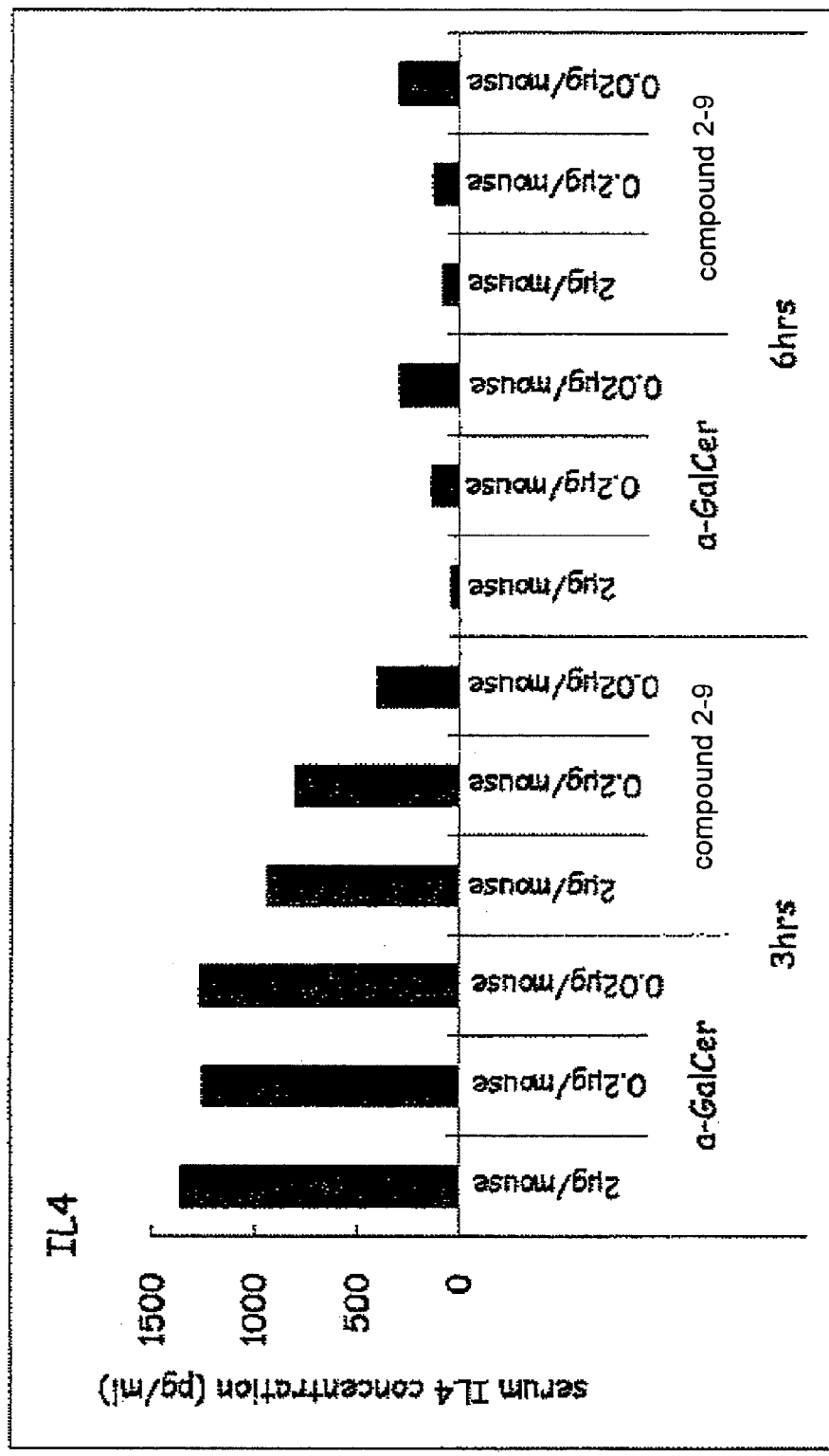
FIG. 7 shows the concentration of IL-4 in the serum after lapse of indicated time from the administration of synthetic glycolipid to the tail of mouse by intravenous injection.

By a method similar to Experimental Example 1 except that the dose of α-GalCer and compound 2-9 was 2 μg/mouse, 0.2 μg/mouse or 0.02 μg/mouse, the content of IL-4 in the serum after lapse of 3 and 6 hr from the administration of α-GalCer and compound 2-9 was measured. The measurement results (average value) of the IL-4 production level and the standard deviation (STDEV) thereof are shown in FIG. 7.

Figure 9:
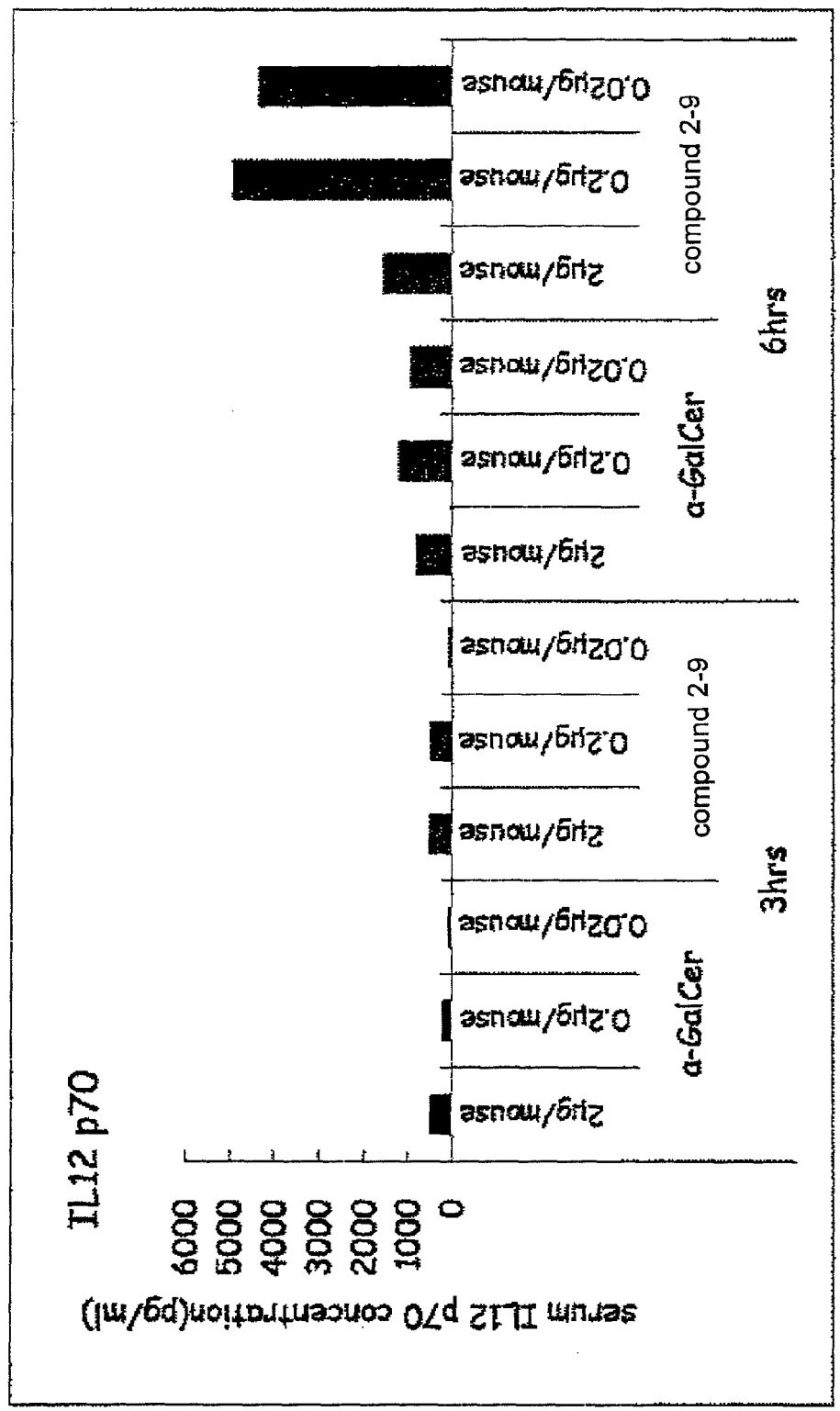
FIG. 9 shows the concentration of IL-12 in the serum after lapse of indicated time from the administration of synthetic glycolipid to the tail of mouse by intravenous injection.

By a method similar to Experimental Example 1 except that the dose of α-GalCer and compound 2-9 was 2 μg/mouse, 0.2 μg/mouse or 0.02 μg/mouse, the content of IL-12(p70) in the serum after lapse of 3 and 6 hr from the administration of α-GalCer and compound 2-9 was measured. The measurement results (average value) of the IL-12 production level and the standard deviation (STDEV) thereof are shown in FIG. 9.

From the above-mentioned results, compound 2-9 induced production of a larger amount of IFN-γ than α-GalCer even by administration at a lower concentration. In addition, compound 2-9 induced production of IL-12 in the same level as or up to 4-fold level as compared with α-GalCer. On the other hand, the production level of IL-4 decreased as the dose of compound 2-9 was reduced. Therefrom it was shown that compound 2-9 selectively induced production of IFN-γ in larger amounts as compared to α-GalCer even by administration at a lower concentration.

This application is based on a patent application No. 2008-079265 filed in Japan, the contents of which are incorporated in full herein.

The invention claimed is:

1. A compound represented by the following formula (1)

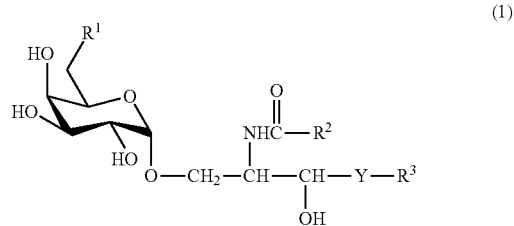

wherein $R^1$ is a hydrogen atom, an alkyl group having a carbon number of 1 to 7, an alkoxy group having a carbon number of 1 to 6 or a halogen atom, $R^2$ and $R^3$ are each independently a substituted or unsubstituted hydrocarbon group having a carbon number of 1 to 28, and Y is —$CH_2$—, —CH(OH)— or —CH=CH—, provided that when $R^1$ is a hydrogen atom, then $R^2$ is a substituted or unsubstituted hydrocarbon group having a carbon number of 24 to 28, or a salt thereof.

2. The compound according to claim 1, wherein $R^1$ is a hydrogen atom, a methyl group, a methoxy group, an ethoxy group, an n-propyloxy group or a fluorine atom, or a salt thereof.

3. The compound according to claim 1, wherein $R^1$ is an alkyl group having a carbon number of 1 to 7, an alkoxy group having a carbon number of 1 to 6 or a halogen atom and $R^2$ is a substituted or unsubstituted alkyl group having a carbon number of 1 to 28, or $R^1$ is a hydrogen atom and $R^2$ is a substituted or unsubstituted alkyl group having a carbon number of 24 to 28, or a salt thereof.

4. The compound according to claim 1, wherein $R^3$ is a substituted or unsubstituted alkyl group having a carbon number of 1 to 28, or a salt thereof.

5. The compound according to claim 1, wherein Y is —CH(OH)—, or a salt thereof.

6. A compound represented by the following formula (2)

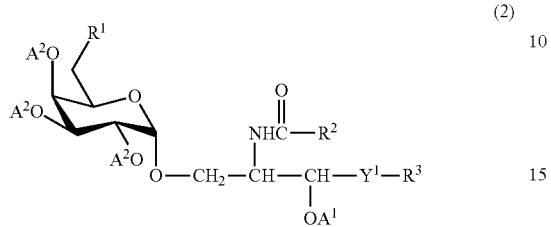

(2)

wherein $R^1$ is a hydrogen atom, an alkyl group having a carbon number of 1 to 7, an alkoxy group having a carbon number of 1 to 6 or a halogen atom, $R^2$ and $R^3$ are each independently a substituted or unsubstituted hydrocarbon group having a carbon number of 1 to 28, $Y^1$ is —CH$_2$—, —CH(OA$^1$)- or —CH=CH—, A$^1$ is a hydrogen atom or a hydroxyl-protecting group, and A$^2$ is a hydroxyl-protecting group, provided that when $R^1$ is a hydrogen atom, then $R^2$ is a substituted or unsubstituted hydrocarbon group having a carbon number of 24 to 28, or a salt thereof.

7. The compound according to claim 2, wherein $R^1$ is a hydrogen atom, a methyl group, a methoxy group, an ethoxy group, an n-propyloxy group, or a fluorine atom, and $R^2$ is a substituted or unsubstituted alkyl group having a carbon number of 1 to 28, or $R^1$ is a hydrogen atom and $R^2$ is a substituted or unsubstituted alkyl group having a carbon number of 24 to 28, or a salt thereof.

8. The compound according to claim 2, wherein $R^3$ is a substituted or unsubstituted alkyl group having a carbon number of 1 to 28, or a salt thereof.

9. The compound according to claim 2, wherein Y is —CH(OH)—, or a salt thereof.

10. A method for immunostimulation, comprising administering an effective amount of a compound represented by the following formula (1)

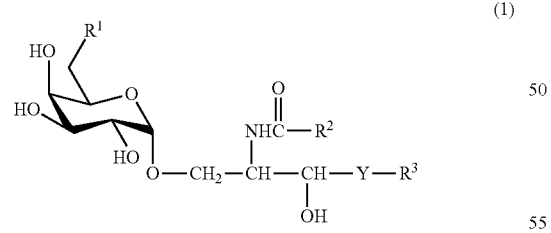

(1)

wherein $R^1$ is a hydrogen atom, an alkyl group having a carbon number of 1 to 7, an alkoxy group having a carbon number of 1 to 6 or a halogen atom, $R^2$ and $R^3$ are each independently a substituted or unsubstituted hydrocarbon group having a carbon number of 1 to 28, and Y is —CH$_2$—, —CH(OH)— or —CH=CH—, provided that when $R^1$ is a hydrogen atom, then $R^2$ is a substituted or unsubstituted hydrocarbon group having a carbon number of 24 to 28, or a salt thereof, to a subject in need thereof, thereby effecting immunostimulation in the subject.

11. A method for inducing selective IFN-γ production, comprising administering an effective amount of a compound represented by the following formula (1)

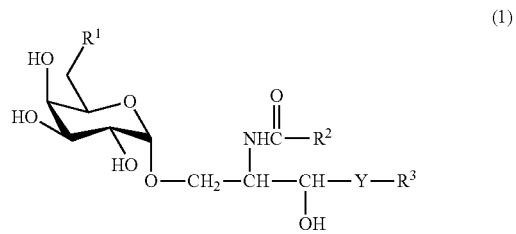

(1)

wherein $R^1$ is a hydrogen atom, an alkyl group having a carbon number of 1 to 7, an alkoxy group having a carbon number of 1 to 6 or a halogen atom, $R^2$ and $R^3$ are each independently a substituted or unsubstituted hydrocarbon group having a carbon number of 1 to 28, and Y is —CH$_2$—, —CH(OH)— or —CH=CH—, provided that when $R^1$ is a hydrogen atom, then $R^2$ is a substituted or unsubstituted hydrocarbon group having a carbon number of 24 to 28, or a salt thereof, to a subject in need thereof, thereby inducing selective IFN-γ production in the subject.

12. A method for treating cancer, comprising administering an effective amount of a compound represented by the following formula (1)

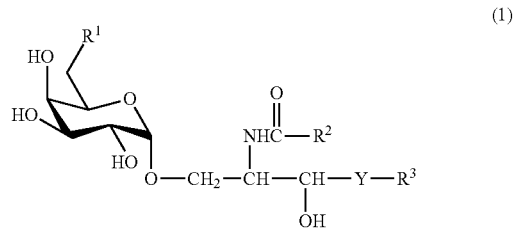

(1)

wherein $R^1$ is a hydrogen atom, an alkyl group having a carbon number of 1 to 7, an alkoxy group having a carbon number of 1 to 6 or a halogen atom, $R^2$ and $R^3$ are each independently a substituted or unsubstituted hydrocarbon group having a carbon number of 1 to 28, and Y is —CH$_2$—, —CH(OH)— or —CH=CH—, provided that when $R^1$ is a hydrogen atom, then $R^2$ is a substituted or unsubstituted hydrocarbon group having a carbon number of 24 to 28, or a salt thereof, to a subject in need thereof, thereby treating cancer in the subject.

* * * * *